United States Patent
Chui et al.

(10) Patent No.: US 6,538,634 B1
(45) Date of Patent: Mar. 25, 2003

(54) APPARATUS FOR THE SIMULATION OF IMAGE-GUIDED SURGERY

(75) Inventors: Chee-Kong Chui, Singapore (SG); Percy Chen, Singapore (SG); Yaoping Wang, Singapore (SG); Marcelo H. Ang, Jr., Singapore (SG); Yiyu Cai, Singapore (SG); Koon-Hou Mak, Singapore (SG)

(73) Assignees: Kent Ridge Digital Labs (SG); The National University of Singapore (SG); Tan Tock Seng Hospital Pte Ltd. (SG)

(*) Notice: Subject to any disclaimer, the term of this patent is extended or adjusted under 35 U.S.C. 154(b) by 0 days.

(21) Appl. No.: 09/215,407

(22) Filed: Dec. 18, 1998

(51) Int. Cl.[7] .................................................. G09G 5/00
(52) U.S. Cl. ..................... 345/156; 434/262; 434/267
(58) Field of Search ........................ 345/156, 161, 345/184, 157, 158, 165, 166; 434/262, 265, 267, 278, 307 R, 365; 606/1, 205, 206

(56) References Cited

U.S. PATENT DOCUMENTS

| | | |
|---|---|---|
| 5,382,885 A | 1/1995 | Salcudean et al. |
| 5,576,727 A | 11/1996 | Rosenberg et al. |
| 5,587,937 A | 12/1996 | Massie et al. |
| 5,589,828 A | 12/1996 | Armstrong |
| 5,609,607 A | 3/1997 | Hechtenberg et al. |
| 5,625,576 A | 4/1997 | Massie et al. |
| 5,629,594 A | 5/1997 | Jacobus et al. |
| 5,766,016 A | 6/1998 | Sinclair et al. |
| 5,800,179 A | 9/1998 | Bailey |
| 5,807,377 A | 9/1998 | Madhani et al. |
| 5,808,665 A | 9/1998 | Green |
| 5,821,920 A | 10/1998 | Rosenberg et al. |
| 6,024,576 A * | 2/2000 | Bevirt et al. ............... 434/262 |
| 6,037,927 A * | 3/2000 | Rosenberg .................. 345/156 |
| 6,038,488 A | 3/2000 | Barnes et al. ............... 700/161 |

OTHER PUBLICATIONS

Barnes, S.Z. et al., "The Realization of a Haptic (Force Feedback) Interface Device for the Purpose of Angioplasty Surgery Simulation," Journal of Biomedical Sciences Instrumentation, vol. 33, pp. 19–24, 1997.

Hunter, I. W. et al., A Teleoperated Microsurgical Robot and Associated Virtual Environment for Eye Surgery, Presence, vol. 2, No. 4, pp. 265–280, Fall 1993.

(List continued on next page.)

Primary Examiner—Dennis-Doon Chow
(74) Attorney, Agent, or Firm—Holland & Knight LLP

(57) ABSTRACT

An apparatus for use in simulated image guided surgery comprises a positional transducer, clamping means located proximate to the transducer, and a processor. The transducer is responsive to a thin flexible member that can be manipulated by a user, and produces signals representative of displacement and rotation of the thin flexible member. The clamping means responds to a controlling signal to apply a predetermined variable clamping force to the flexible member. The processor receives these displacement and rotation signals, and is programmed to plot the path of the flexible member therefrom as it is manipulated by the user. Additionally, the processor produces the controlling signal to the clamping means in response to the instantaneous position along the path. The processor may be coupled to a display device for displaying an image of the instantaneous position of the flexible wire therealong, or other information. The invention also includes a related method for the simulation of image guided surgery. Embodiments of the invention can be used to simulate the manual positioning of a catheter and guidewire, as well as the haptic forces exerted by the user's hand and fingers in that positioning, or can simulate the process of balloon angioplasty, including stent deployment.

38 Claims, 14 Drawing Sheets

OTHER PUBLICATIONS

Howe, R. D. et al., "Remote Palpation Technology," IEEE Engineering in Medicine and Biology, pp. 318–323, May/Jun. 1995.

Playter, R. et al., "A Virtual Surgery Simulator Using Advanced Haptic Feedback," Journal of Minimally Invasive Therapy and Allied Technologies, vol. 6, pp. 117–121, 1997.

Langrana, N. A. et al., "Dynamic Force Feedback in a Virtual Knee Palpation," Artificial Intelligence in Medicine, pp. 321–333, vol. 6, 1994.

Rosen, J. M. et al., "Virtual Reality and Surgery," Computer–Integrated Surgery, MIT Press, Cambridge, MA, USA, pp. 231–243, 1996.

* cited by examiner

1 - LEFT MAIN TRUNK
2 - LEFT ANTERIOR DESCENDING BRANCH (PROXIMAL)
3 - LEFT ANTERIOR DESCENDING BRANCH (MID)

APPARATUS FOR THE SIMULATION OF IMAGE-GUIDED SURGERY

BACKGROUND OF THE INVENTION

1. Field of the Invention

The present invention relates to the field of image-guided surgery, and particularly to apparatus for the simulation of such surgery, such as may be used for pre-planning, teaching or research purposes.

2. Background

Minimally invasive therapeutic procedures, including surgery and interventional radiology, reduce patient discomfort, hospital stay, and medical costs. The socioeconomic impact of compensation for lost work time is also reduced. Interventional radiology began as a tool for diagnosing and treating vascular disease (defects, notably narrowing in arteries) by catheters that move along the blood vessel and guided by fluoroscopy. The interventional radiologist uses a catheter passed into a blood vessel through a puncture in the skin to gain internal access to the site of disease. The catheter is then used as a conduit to pass therapeutic devices to treat the condition. Its principle advantages include direct surgical exposure by cutting through the flesh is not needed, and many of the procedures are performed on an outpatient basis. This reduces cost and the discomfort to the patient, as well as the time of convalescence.

Such procedures are typically carried out in a cardiac CathLab, where a physician wishes to assess the functions of the heart and coronary artery anatomy, or to perform procedures such as coronary angioplasty.

Most radiology yields recorded images: 2D X-ray film, or 3D CAT/MRI scans. "Live" radiology (fluoroscopy) that yields current images of a changing situation allows the radiologist to work with its guidance. Interventional radiology is the specialty in which the radiologist utilizes "live" radiologic images to perform therapeutic, as opposed to only diagnostic procedures. Interventional radiologists currently rely on the real-time fluoroscopic 2D images, available as analog video or digital information viewed on video monitors.

But these procedures involve delicate and coordinated hand movements, spatially unrelated to the view on a video monitor of the remotely controlled surgical instruments. Depth perception is lacking on the flat video display, and it may be hard to learn to control the tools through the spatially arbitrary linkage. A mistake in this difficult environment can be dangerous. Therefore, a high level of skill is required, and realistic training of these specialists is difficult. In addition, there is no direct engagement of the depth perception of the radiologist, who must make assumptions about the patient's anatomy to deliver therapy and assess the results.

Medical simulators that can be used to train such medical specialists have significant potential in reducing healthcare costs through improved training, better pre-treatment planning, and more economic and rapid development of new medical devices. They shift the traditional see one, do one, teach one paradigm of medical education to one that is more experienced-based. Hands-on experience becomes possible in training, before direct patient involvement that will carry a significant risk.

Image-guided procedures, such as vascular catheterization, angioplasty, and stent placement, are specially suited for simulation because they typically place the physician at-a-distance from the operative site manipulating surgical instruments and viewing the procedures on video monitors.

In the medical field of simulation there are a number of technical challenges to overcome. The difficulties in providing hand-feeling haptic device and in creating a realistic simulation environment with a close-to-life resemblance of the operative site for controlling and manipulating the movements of simulated medical equipment has actually dampened the development of the simulators for image-guided surgery. The haptic "feel", for example, gives the surgeons another measure, beside the fluoroscopic image displayed on the video monitor, to navigate the catheter into a desired vessel. It is therefore extremely important to provide a haptic device with an interactive hand-feeling capability in an image-guided simulation system.

There are a few known simulation devices developed for this purpose. In U.S. Pat. No. 5,609,607, issued on Sep. 26, 1994, Hechtenberg et al have proposed an approach to build a device for modeling or simulating the sense of touch in a surgical instrument. It aims to provide the feeling of tissue-like contact on a layer member for surgical simulation.

Researchers at Georgia Tech have created a device incorporating virtual reality to simulate the look and feel of eye surgery, described in U.S. Pat. No. 5,766,016 (Sinclair et al), issued on Jun. 16, 1998. It has linear tactile feedback for real-time feel of tool-tissue interaction through three sets of levers and hinges to three servo-motors which collectively generate a resistive force along any direction.

In an article titled "A virtual surgery simulator using advanced haptic feedback", published in *Journal of Minimally Invasive Therapy and Allied Technologies*, Volume 6/2, pp 117–121, Playter et al describe a method to provide a sense of touch. Users hold real medical instruments and touch, grasp, and suture two simulated tube organs as they practice end-to-end anastomosis procedures.

Barnes et al also proposed a haptic (force feedback) interface device for the purpose of angioplasty surgery simulation. This is described in an article titled "The realization of a haptic (force feedback) interface device for the purpose of angioplasty surgery simulation", in *Journal of Biomedical Sciences Instrumentation*, Volume 33, pp 19–24.

There is a need, not satisfied by the prior art, to provide accurate determination of the actual motions and forces imparted upon the proximal portion of the navigating devices (e.g. catheters, guidewires, etc) and, at the same time, to create a realistic simulation of image manipulation and device control.

SUMMARY OF THE INVENTION

It is an object of the invention to overcome, or at least ameliorate, one or more of the disadvantages or deficiencies in the prior art.

The invention in one aspect provides apparatus for use in simulated image guided surgery, comprising:

positional transducer means responsive to a thin flexible member that can be manipulated by a user, the transducer means producing signals representative of displacement and rotation of said flexible member;

clamping means located proximate said transducer means, and operable to respond to a controlling signal to apply a predetermined variable clamping force to the flexible member; and processor means receiving said displacement and rotation signals, and programmed to plot the path of the flexible member therefrom as it is manipulated by the user, and to produce said controlling signal in response to the instantaneous position along the path.

The invention in another aspect further provides a system for the simulation of image guided surgery, comprising:

a thin flexible member that can be manipulated by a user;

positional transducer means responsive to said flexible member to produce signals representative of displacement and rotation of said flexible member;

clamping means located proximate said transducer means, and operable to respond to a controlling signal to apply a predetermined variable clamping force to the flexible member;

processor means receiving said displacement and rotation signals, and programmed to plot the path of the flexible member therefrom as it is manipulated by the user and to produce said controlling signal in response to the instantaneous position along the path taken form a predetermined simulation of the path; and display means, coupled to the processor means, to display an image of at least the instantaneous position of the flexible wire therealong.

The invention in another aspect further includes a method for the simulation of image guided surgery, the method comprising the steps of:

transducing the displacement and rotation of a thin flexible member manipulated by a user;

plotting the path of the flexible member along a simulated path representing vasculature;

user selectably displaying an image of the instantaneous position of the flexible member along the path and/or a portion of the path; and applying a predetermined variable clamping force to the flexible member in accordance with the instantaneous position of the flexible member.

Embodiments of the invention can be used to simulate the manual positioning of a catheter and guidewire, as well as the haptic forces exerted by the user's hand and fingers in that positioning. Other embodiments can simulate the process of balloon angioplasty, including stent deployment.

Embodiments of the invention offer a number of advantages in that a realistic simulation of image guided surgery is provided whereby all the input variables or controls that are experienced in real image guided surgery are included. Particularly a force feedback mechanism to provide a representative tactile sense to the user is achieved, and this assists in the training or pre-planning of surgery.

BRIEF DESCRIPTION OF THE DRAWINGS

The various embodiments of the invention will be described with reference to the accompanying drawings, in which.

DESCRIPTION OF PREFERRED EMBODIMENTS

As used in this specification, a reference to "a thin flexible member" is to be understood as referring to a catheter, guidewire, stent device, or other such device inserted into a blood vessel.

Figure 1:
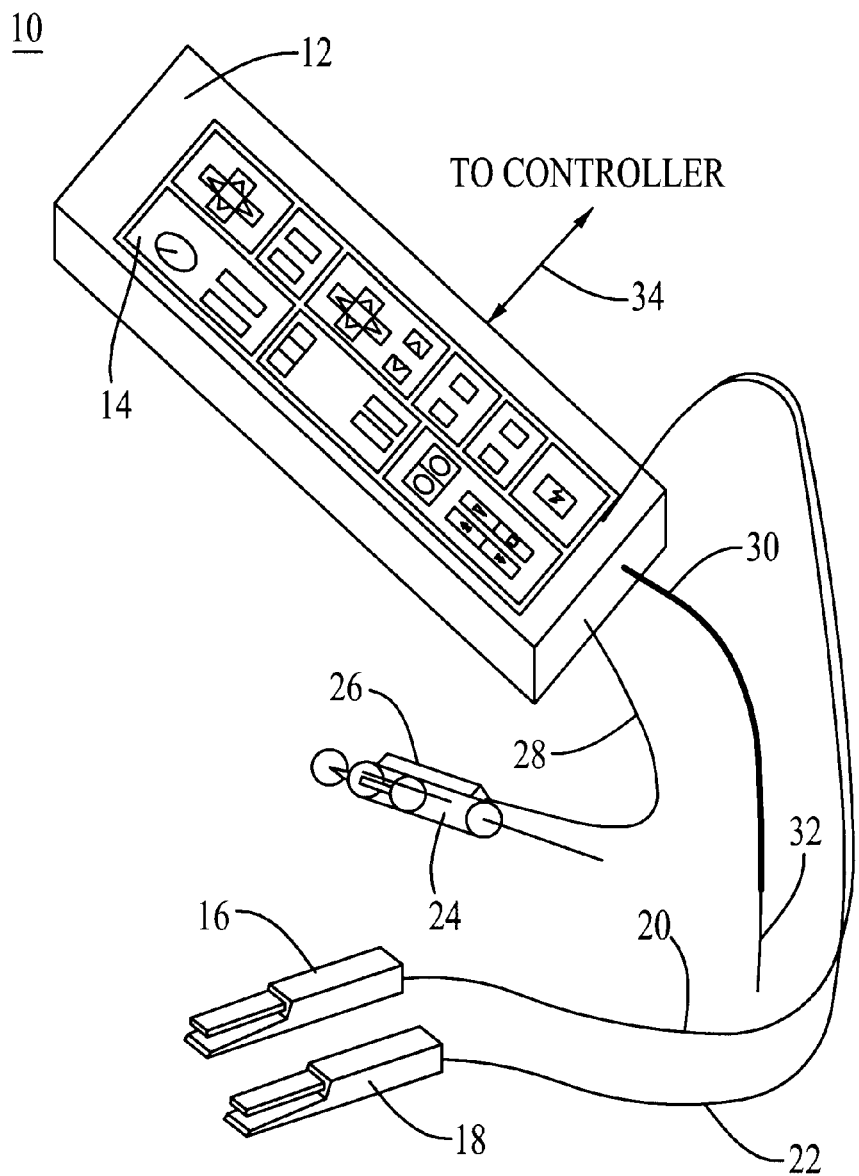
FIG. 1 shows a perspective view of TiC apparatus.

FIG. 1 shows a perspective view of a Tactile and Image Control (TiC) apparatus (10). The apparatus includes a casing (12) carrying a control panel (14), that will be described in further detail presently. Two foot switches (16,18) are electrically connected to an interface circuit within the casing (12) via respective electrical cables (20, 22). Also external of the casing (12) is a simulated syringe (24) having connection to a slide potentiometer (26), in turn coupled to an interface circuit within the casing (12) by an electrical cable (28). Further, there is a catheter (sleeve) (30) extending from the casing (12) which can be manually manipulated to be inserted into, and withdrawn from the casing (12). The catheter (30) carries a guidewire (32) that similarly can be mechanically manipulated to be inserted or retracted. The circuits within the casing (12) also have connection to a data link (34) having connection to a external controller (not shown). The power supply to the TiC apparatus is not shown.

In use, the TiC apparatus (10) is operated in conjunction with a controller and a surgical simulation system in combination simulating, capturing and manipulating fluoroscopic image views in an image guided procedure. This includes measuring the user's manual positioning of the catheter and guidewire, as well as the haptic forces exerted by the user's hands and fingers.

Figure 2:
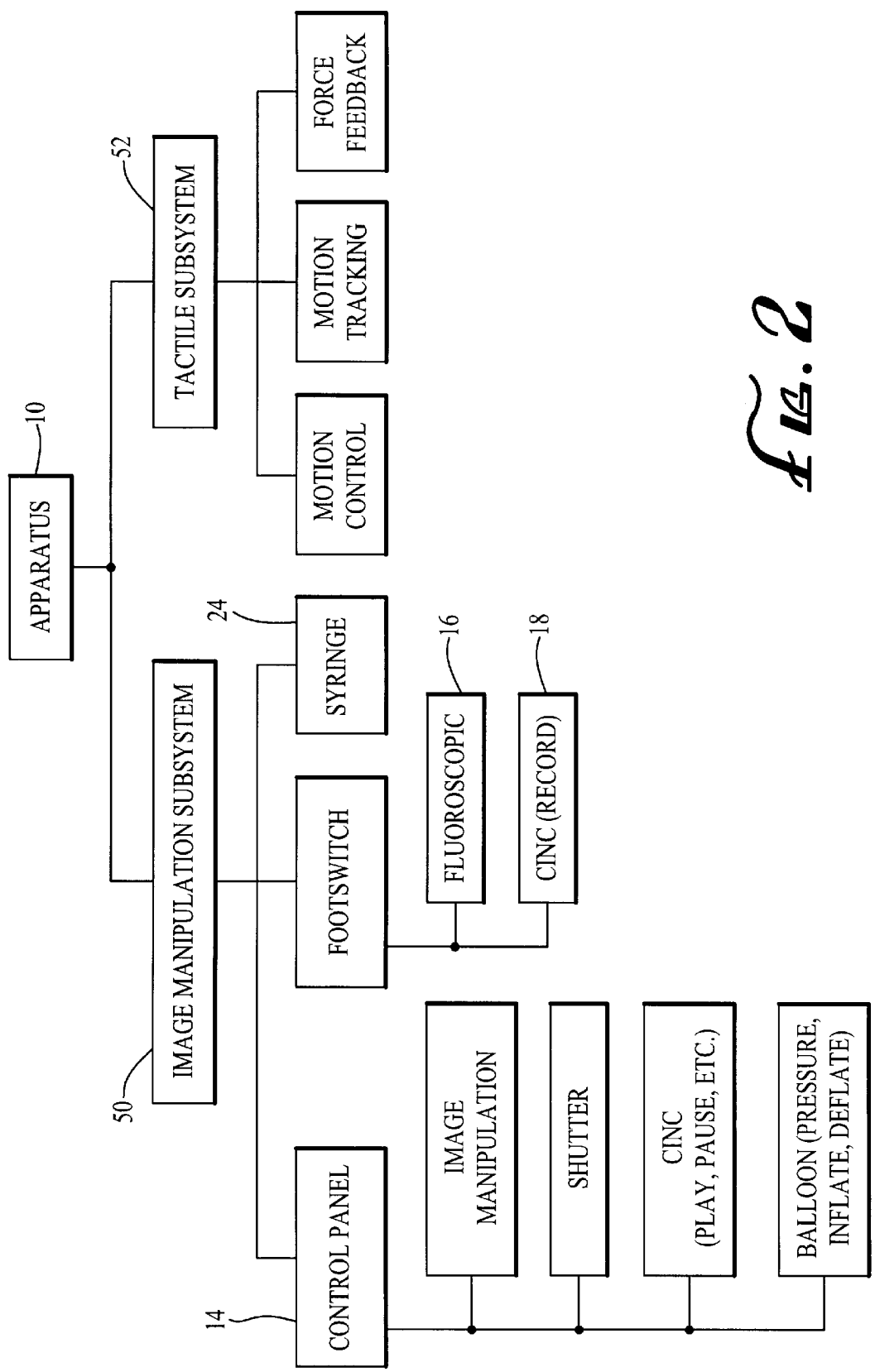
FIG. 2 is a block diagram of the TiC apparatus.

FIG. 2 is a block diagram of the TiC apparatus (10) components in a hierarchical order. There is a first image manipulation subsystem (50) constituted by the interface circuit (54), the control panel (14), the foot switches (16,18) and the syringe (24). The control panel (14) includes controls for image manipulation, shutter control, cine control and balloon control. There is a second, tactile subsystem (52) that has an interface circuit (56) and the functions of motion control, motion tracking and force feedback. The functions of these elements will be presently described.

Figure 3A:
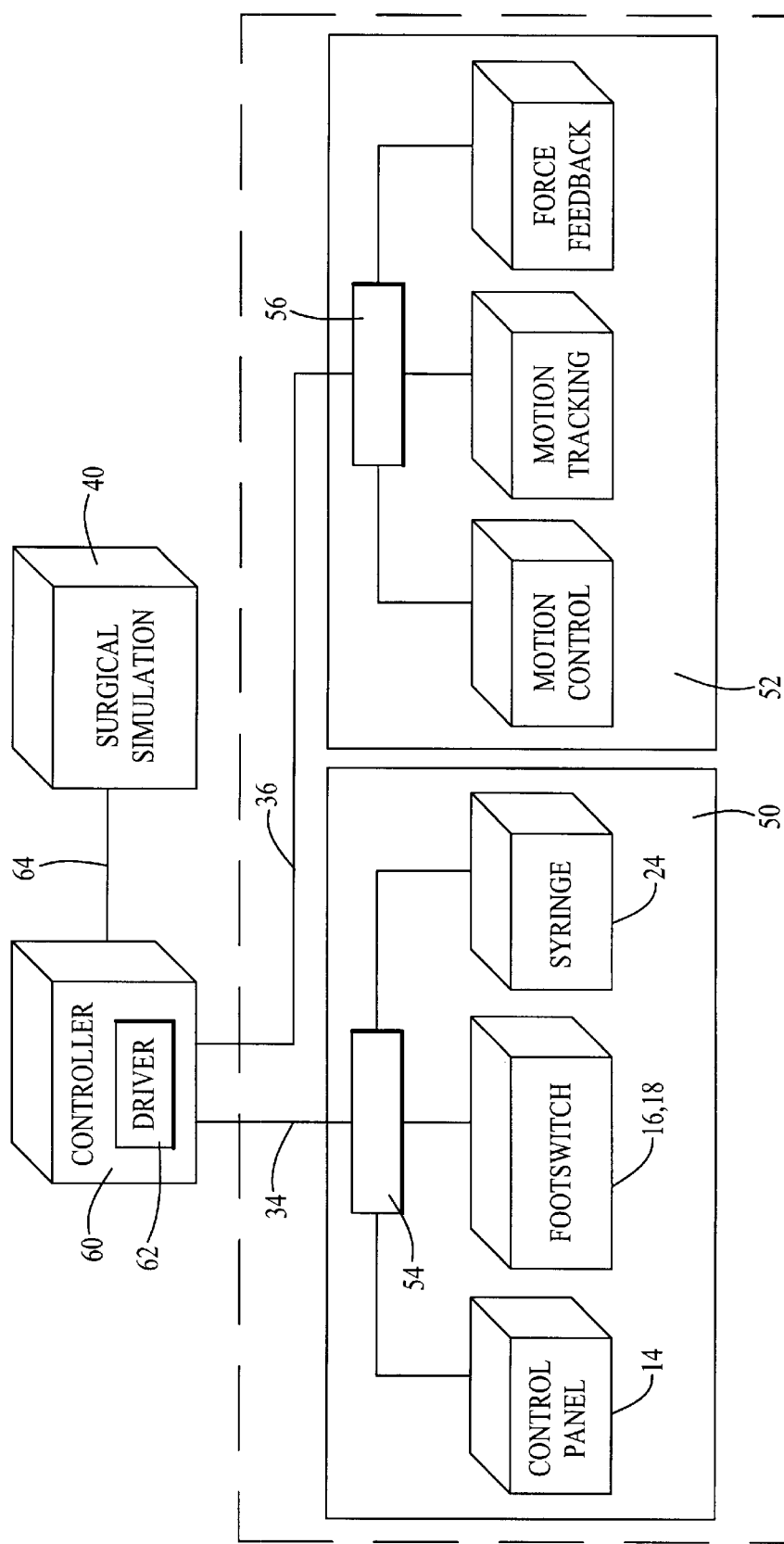
FIG. 3a is a block diagram showing a composite simulation system.

FIG. 3a is a block diagram representing the system hardware architecture. The TiC apparatus (10) has connection to a controller (60) in the form of a personal computer, that includes a driver subcircuit (62). The data link (34) connects the driver subcircuit with the respective interface circuits (54,56). A data link (64) is also present from the controller (60) to the surgical simulation apparatus (40). The surgical simulation apparatus (40) typically be implemented on a workstation, such as the Silicon Graphics IRIS-4D series workstation. The data link (64) should carry at least 3 serial lines, that will be further described presently.

Figure 3B:
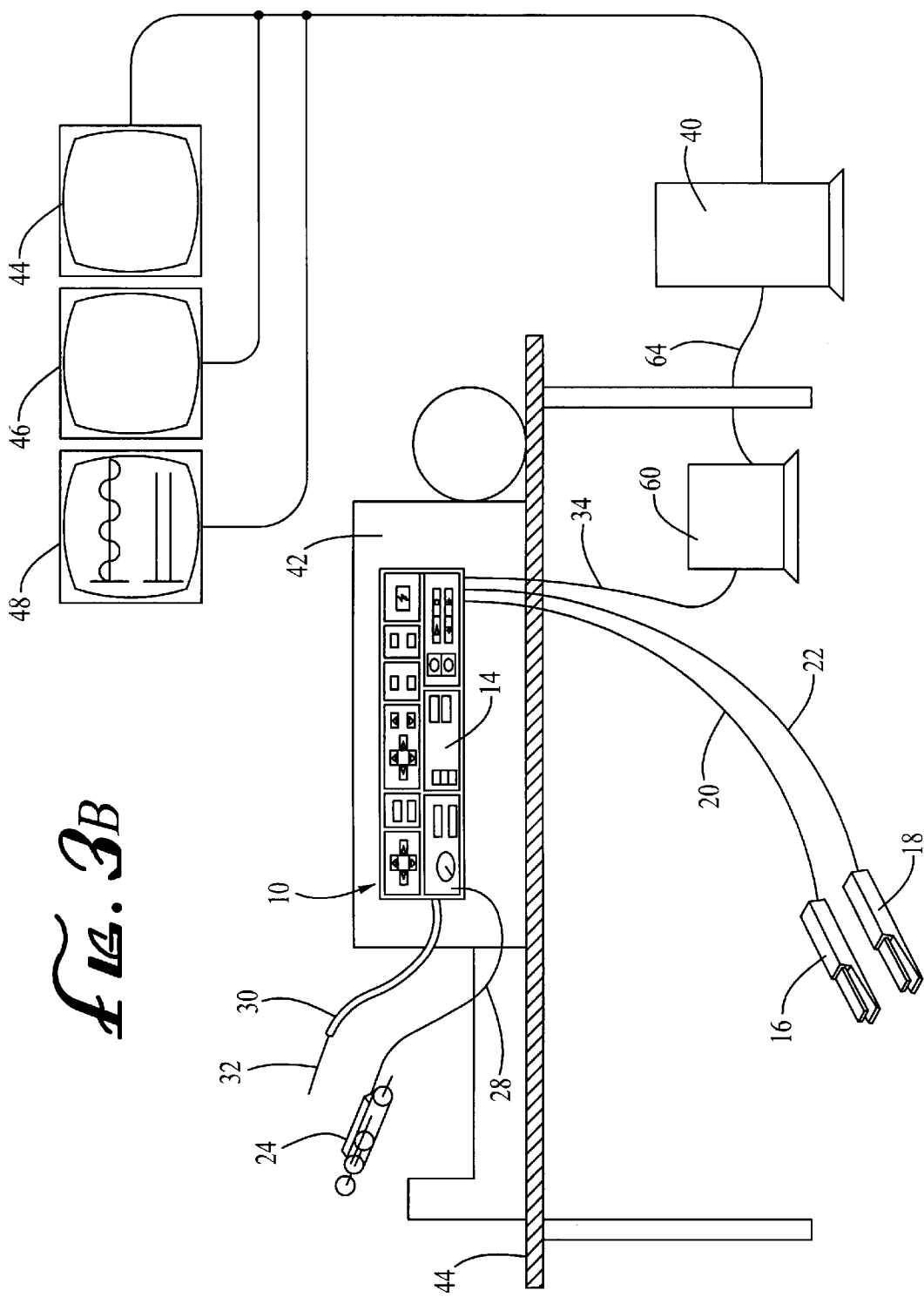
FIG. 3b is another representation of the simulation system.

FIG. 3b shows a general arrangement for a CathLab simulation system employing the TiC apparatus (10). The TiC apparatus is conveniently located as a component of a manikin (42) laid on a table (44) in a manner similar to an operating theatre table.

The location of the input devices to the TiC apparatus (10) also is shown, including the catheter (30), guidewire (32), syringe (24) and foot switches (16,18). The controller (60) is a floor-mounted personal computer, having connection to a workstation (40). The workstation (40) further has connection with three video monitors. The first monitor (44) provides a fluoroscopic image which is obtained by subjecting a patient to x-ray exposure and contrast dye injections. The second monitor (46) presents the physician with a roadmap image, which is also known as a cine image. Cine images are recorded fluoroscopic images, and as the name suggests, provide the physician with an indication of the path to be taken in inserting the catheter (30) and/or guidewire (32). The third monitor (48) provides usual biomedical signals such as ECG, respiration, x-ray procedure and duration of the procedure. The workstation (40) has stored in it fluoroscopic, roadmap and biomedical signals, and is programmed to interact with the TiC apparatus and associated controller (60) to simulate a surgical procedure. Following the fluoroscopic and roadmap images, the physician navigates the catheter (30) and the guidewire (32) to the site, and once at that location, the physician can cause inflation of a balloon or deploy a stent to treat the disease segment of the vessel. The TiC apparatus (10) also provides a form of force feedback upon the catheter and guidewire to simulate a physical interaction between those devices and the wall of the vessels through which they pass.

Image Manipulation Subsystem

The image manipulation subsystem (50) simulates capture and manipulation of fluoroscopic image views in an image guided procedure.

The SHUTTER buttons (82) are used to facilitate the shutter operation in an image guided procedure. By opening and closing the vertical and horizontal shutters, the surgeon/radiologist will be able to minimize patient's exposure to X-ray. In the simulation, user first selects the horizontal or vertical shutter to be used, and then depresses the SHUTTER-OPEN and SHUTTER-CLOSE buttons (84,86) to open or close up the chosen shutter.

To inflate or deflate the balloon catheter with BALLOON buttons (88), users have to first set the amount of pressure to be used. A typical range is between 0 and 20 bars for interventional cardiology procedures. The pressure is set using a potentiometer (90) that changes resistance by sliding in a circle.

The group of ROADMAP buttons (92) are used to operate on the cine images captured in an image guided procedure. These buttons feature controls similar to those available in a video panel. It is preferred that there be two simultaneous displays of roadmap or channels reflecting the orthogonal views of the target cases. Activation of the respective channel is controlled using ROADMAP buttons labelled "1" and "2" respectively. The other ROADMAP buttons are used to "play", "stop", "advance" and "reverse" the roadmaps.

The two foot switches (16,18) are respectively used for activation of X-ray for fluoroscopic images, and to record the image sequence as cine images.

Figure 5A:
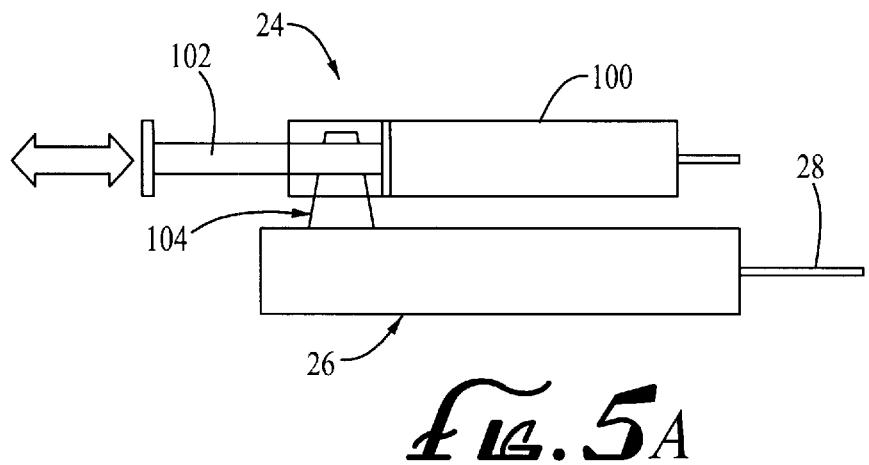
FIGS. 5a and 5b are respectively top and side views of the simulated syringe.
Figure 5B:
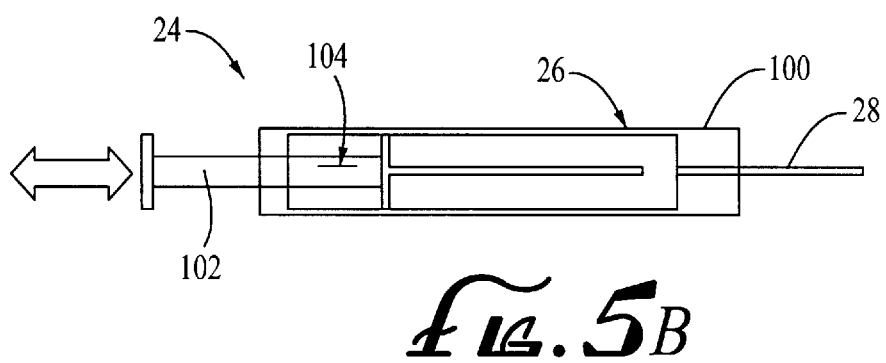

FIGS. 5a and 5b are respectively side and top views of the simulated syringe (24). A conventional syringe body (100) and plunger (102) are used. The plunger (102) has mechanical connection to a tab (104) extending from the potentiometer (26). The potentiometer (26) responds to a change of displacement in the plunger (102) as a variable resistance passed to the controller (60) on the electrical cable (28). The controller also differentiates the variable resistance signal to obtain a rate of change, and thus speed of delivery of the simulated drug or fluid. Thus it is possible to model the simulated dosage injected and the rate of injection.

Figure 5C:
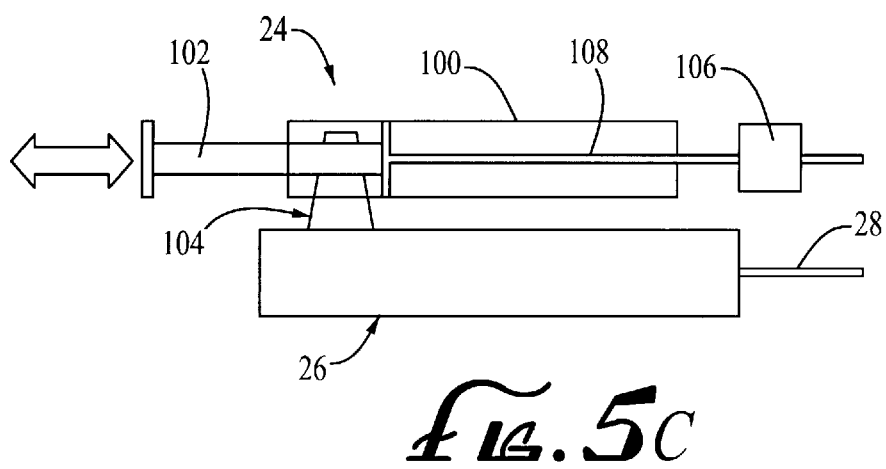
FIG. 5c is an alternative embodiment of the simulated syringe.

FIG. 5c is an alternative embodiment of the simulated syringe. This simulated syringe has been enhanced with force feedback. One end of the syringe is attached to a linear motor. The linear motor is controlled by the controller to provide resistive force when user is injecting drug or fluid in the simulation. We could also use pressure control valve in place of the linear motor. In this case, we have to ensure air tightness in the simulated syringe subsystem.

Figure 6:
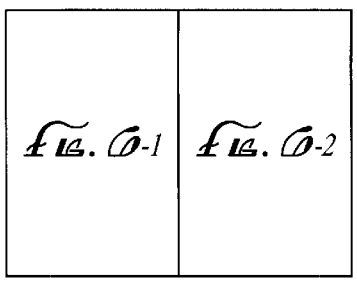
FIG. 6 is a schematic block diagram of the interface circuit.
Figures 1, 6:
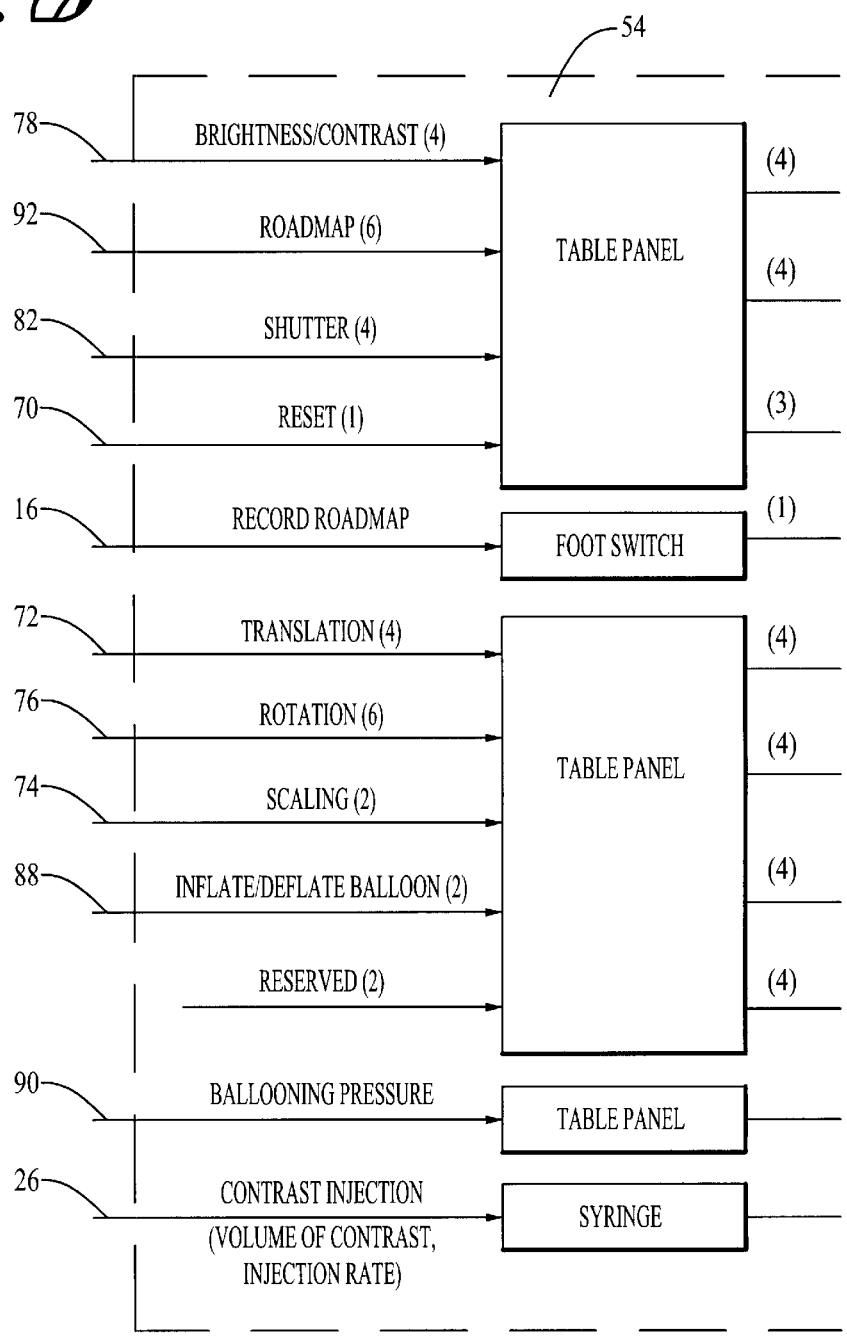

FIG. 6 is a schematic block diagram of the interface circuit (54) of the image manipulation subsystem (50), showing the various inputs from the controls located on the control panel (14). The numbers indicated thereon in parentheses "( )", indicates the number of signals on each signal line. The ballooning pressure signal from the potentiometer (90), and the volume and rate signal from the potentiometer (26) of the catheter (30) are separately passed to the personal computer (60) as analog signals, received by a MIDI port forming a part of the driver sub-circuit (62). The remaining signals pass by a series of multiplexers as digital signals on the data link (34) either to the personal computer's MIDI port or a parallel port.

Tactile Sub-System

The user manipulates the catheter (30) and the guidewire (32) by pushing, pulling and rotating either of them. The movement of the catheter and the guidewire are tracked, and transmitted to the simulation apparatus (40) via the controller (60). Both the catheter (30) and the guidewire (32) are subject to a force feedback mechanism that receives a computed force from the simulation apparatus (40), and directs the force onto either element, thus the manipulation process closely resembles the actual manipulation that would occur in an Operating Room.

Figure 7:
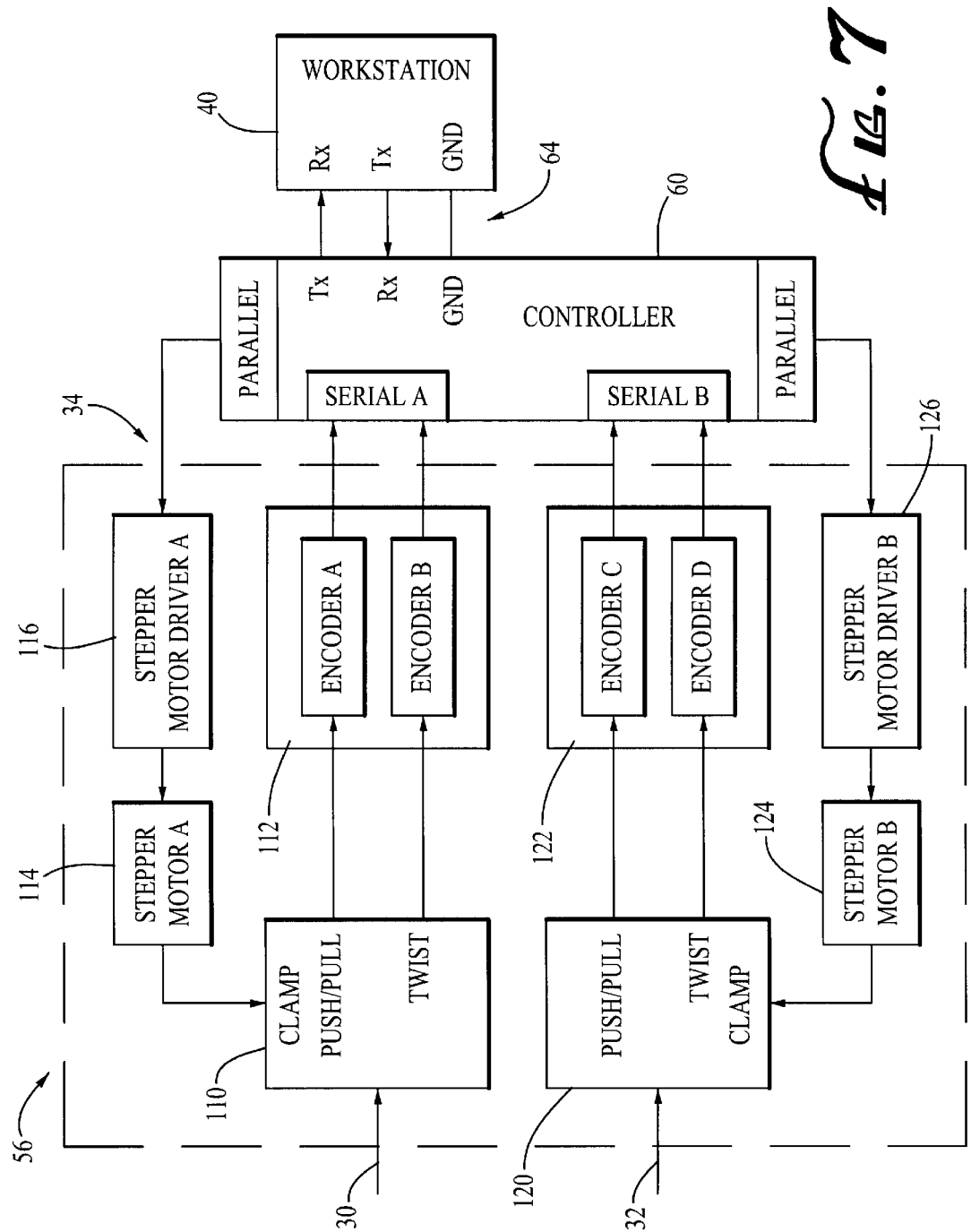
FIG. 7 is a schematic block diagram of the interface circuit.
Figure 8:
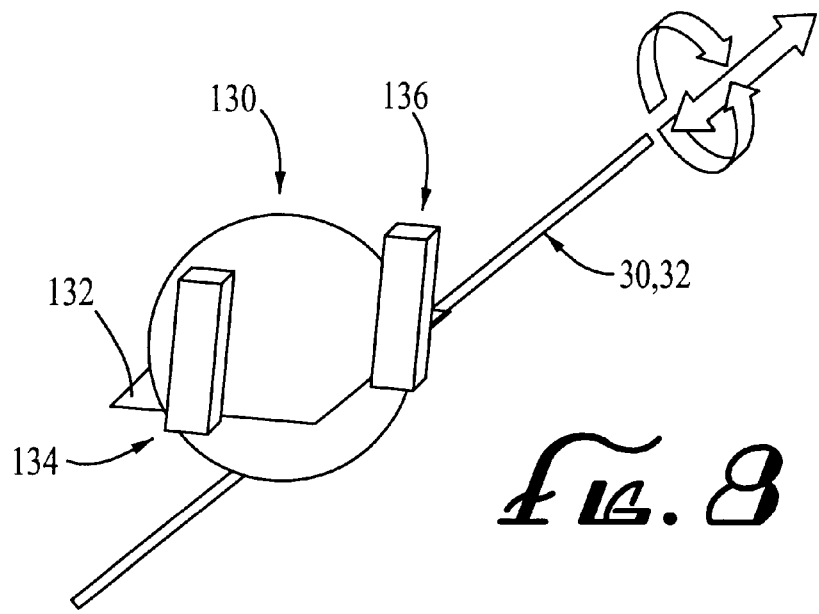

FIG. 7 is a schematic block diagram of the interface circuit (56) of the tactile subsystem (52). The catheter (30) mechanically engages with a transducer (110) that senses and generates separate electrical signals relating to "push-pull and twist", passed to a dual encoder block (112). Encoder A and Encoder B measure the translation and rotational forces of the catheter respectively. These signals are passed on the data link (34) to a serial port of the controller (60). The transducer (110) is a subject of a controlling action by a stepper motor (114), in turn controlled by a motor driver circuit (116) that receives controlling signals from a parallel port of the controller (60).

In a similar way, the guidewire (32) is received by a transducer (120) that produces corresponding "push-pull and twist" signals provided to the controller (60) via a respective encoder element (112). A corresponding stepper motor (124) and motor driver circuit (126) are provided to control the force applied against manipulation of the guidewire (32).

Figures 2, 8:
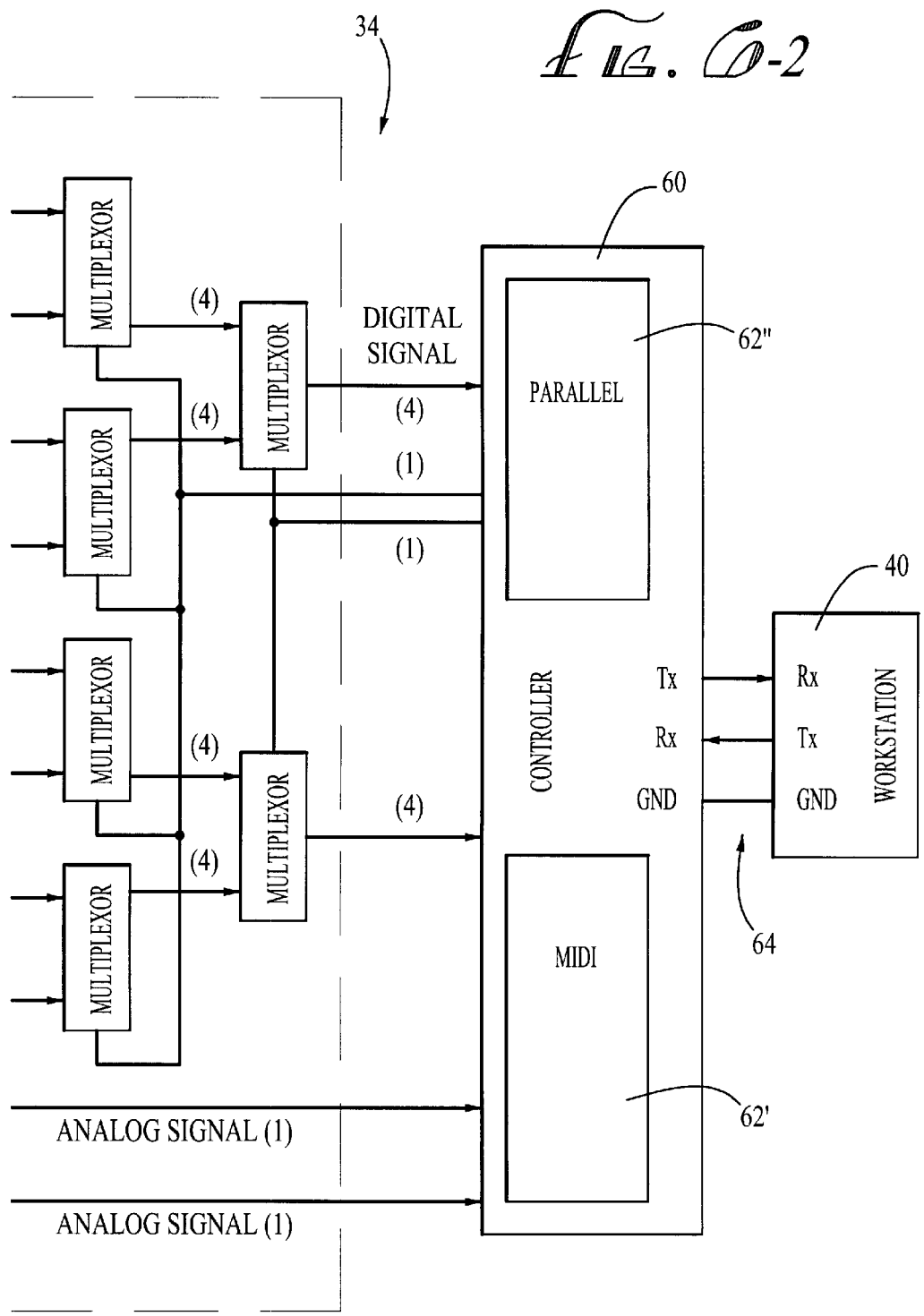
FIG. 8 shows a form of transducer.
Figure 9:
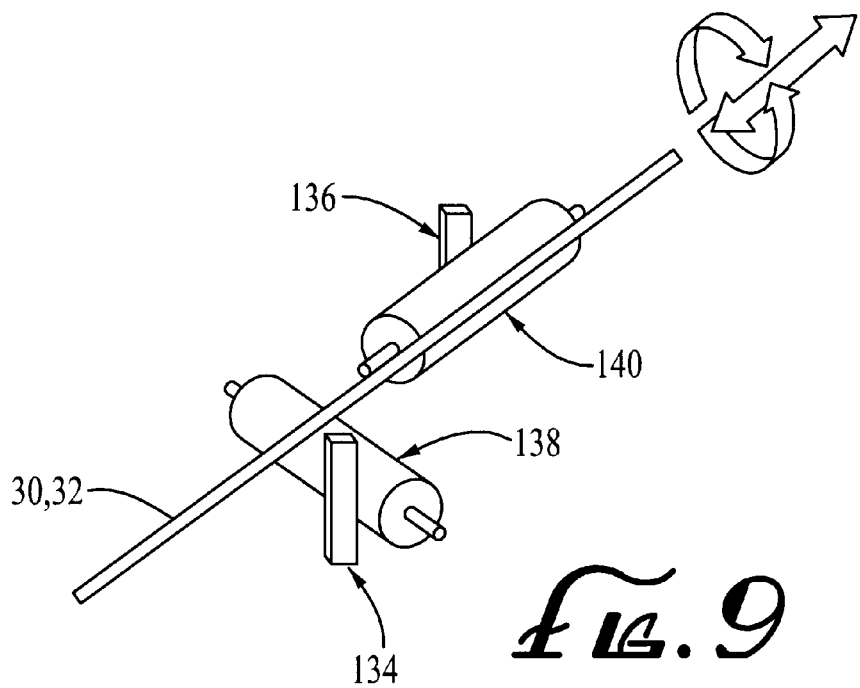
FIG. 9 shows an alternative form of transducer.

FIG. 8 shows one form of a transducer (110,120) and encoder elements (112,122). The encoder elements is embodied as a rolling ball (130) restrained within a mount (132). The encoders (124,136) are of rotary type and respectively respond to translation and rotation. An alternative form of transducer is shown in FIG. 9, where the rolling ball (130) is replaced by two rollers (138,140).

Figure 10:
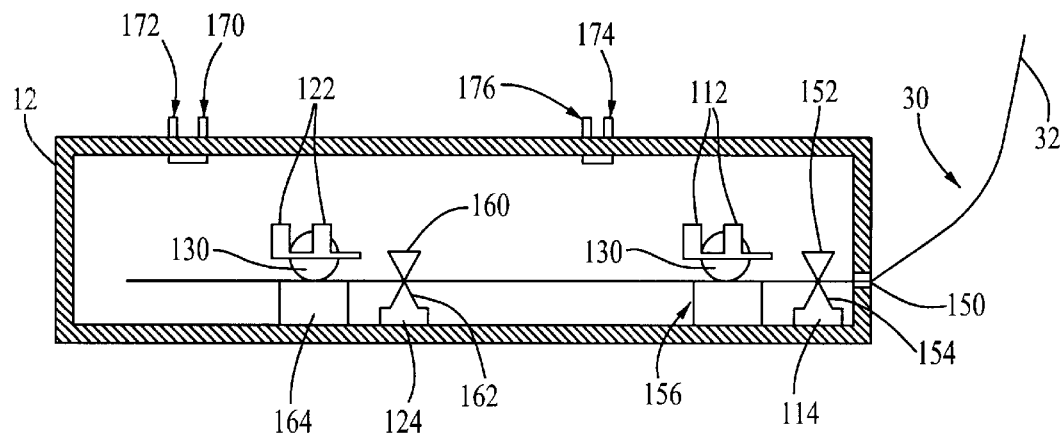
FIG. 10 shows a sectional view of the tactile subsystem.

FIG. 10 shows a mechanical sectional view of the tactile subsystem (52) located within the casing (12), together with relevant ones of the control panel pushbuttons. The catheter (30) and the guidewire (32) enter the casing (12) through a hole (150) in the side wall. The catheter passes through opposed clamp members (152,154) under control of the stepper motor (114), and then between a supporting base (156) and the rolling ball (130). The positioning of the encoder elements (112) also are shown. The guidewire (32) carried within the catheter (30) extends beyond the end of the catheter and similarly passes through a pair of opposed clamp members (160,162) and between a supporting base (164) and the respective rolling ball (130). By this arrangement information concerning the displacement and rotation of both the catheter (30) and the guidewire (32) can be obtained, and independent (and adjustable) resisting force can be applied to other elements by the respective clamp members (152,154,160,162). This is known as force feedback.

Figure 4:
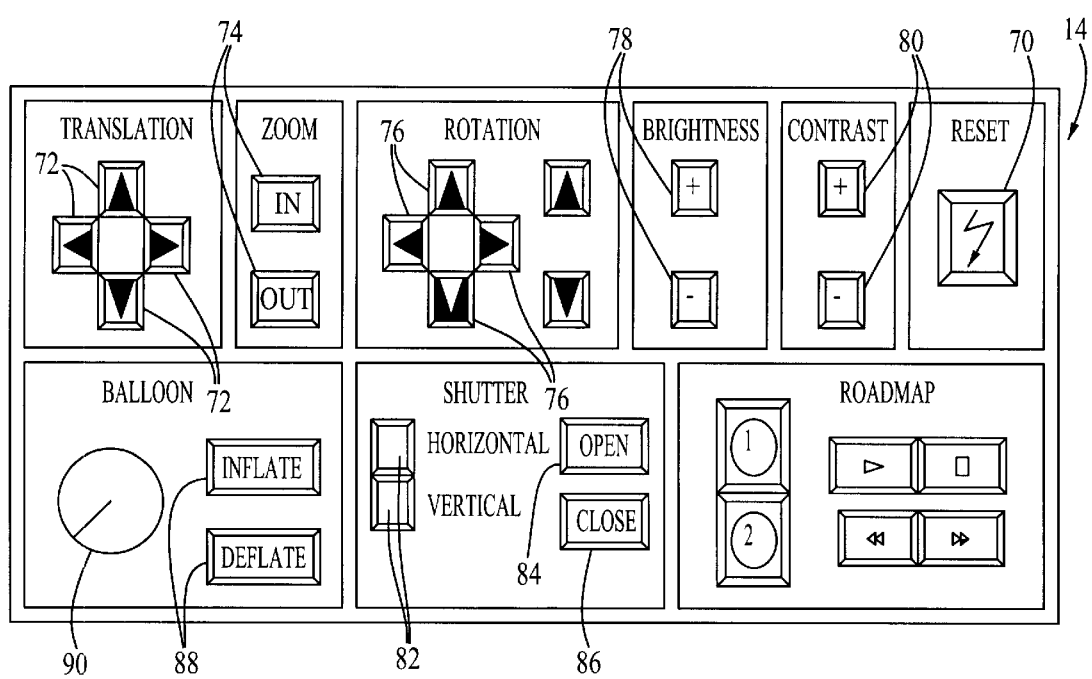
FIG. 4 is a planar view of the control panel.

The four pushbuttons shown mounted from the top face of the casing (12) are specific to the tactile subsystem, and accordingly have not been shown in the earlier representation of the control panel (14) of FIG. 4. These pushbuttons have electrical connection with the controller (60). The two mode pushbuttons (170,172) serve the following purpose: in complicated image guided procedures, more than one set of catheter and guidewire can be inserted at different parts of the human body. For example, a set of catheter and guidewire can be inserted at the neck while having the first set of catheter and guidewire inserted at a femoral location in the patient body. To simulate this arrangement, there are two mode control buttons (INSERTION A and INSERTION B) (170,172) provided to indicate the interventional device that is currently active.

The PAUSE pushbutton (174) and RESUME pushbutton (176) operate to allow positional adjustment of the catheter and guidewire without measurement of the respective translation or twist. This will be necessary given the relatively short length of the catheter (30) and guidewire (32). In reality such elements can be a meter or more in length. By the present arrangement, either the catheter or the guidewire can be manipulated over a certain distance then the PAUSE pushbutton (174) pressed releasing the respective clamps so that both the catheter and the guidewire can be retracted to "reset" their length, then the RESUME pushbutton (176) pressed and the clamp members will be restored and the measurements recommenced.

Figures 11A, 11B:
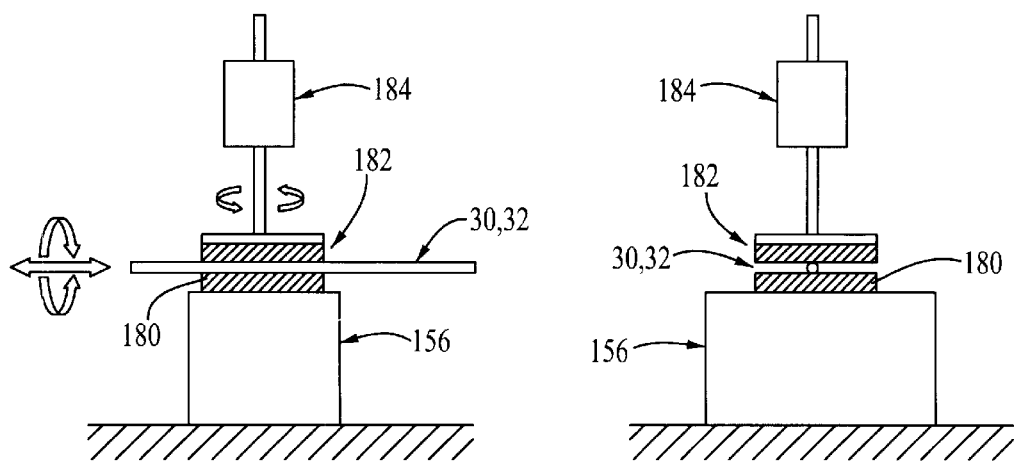
FIGS. 11a and 11b show another embodiment of a force feedback mechanism.

FIGS. 11a and 11b show an alternative embodiment of a force feedback mechanism that can replace the clamps (152,154,160,162) shown in FIG. 10. Here, a base (156) is again provided, on top of which is mounted a fixed cushion (180) over which the catheter (30) or guidewire (32) passes. Translation and rotation of the catheter or guidewire is impeded by an adjustable cushion (182) mounted from a linear stepper motor (184). Such a device provides precise control in a vertical plane meaning that there is no need for other rotary-to-linear conversion such as belts and pulleys, racks and pinions or external wall screws.

Figure 12A:
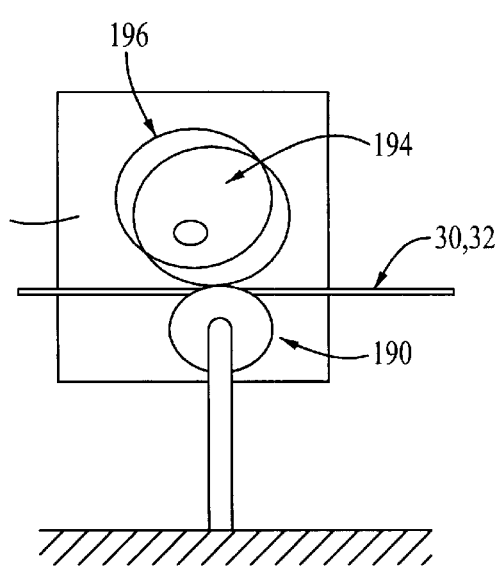
FIGS. 12a and 12b show further embodiments of force feedback mechanisms.
Figure 12B:
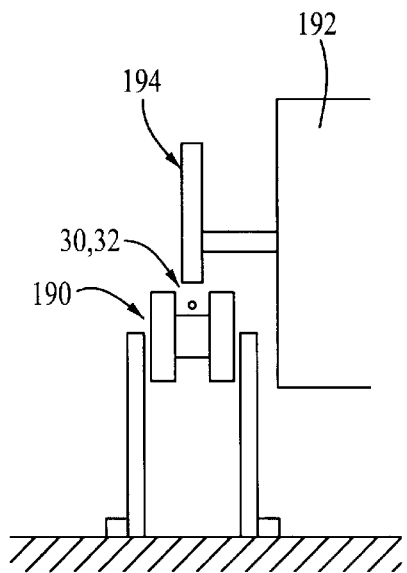

FIGS. 12a and 12b show a yet further embodiment of a force feedback mechanism utilizing a servo motor. The catheter or guidewire passes over a pulley arrangement (190), above which a servo motor (192) is located, and the shaft of which is excentrally attached a wheel (194) carrying on its periphery a rubber coating (196). A force feedback signal from the controller (60) provided to the servo motor (192) causes rotation such that the rubber coating (196) engages the catheter or guidewire, effectively acting as a clamp.

Figure 13:
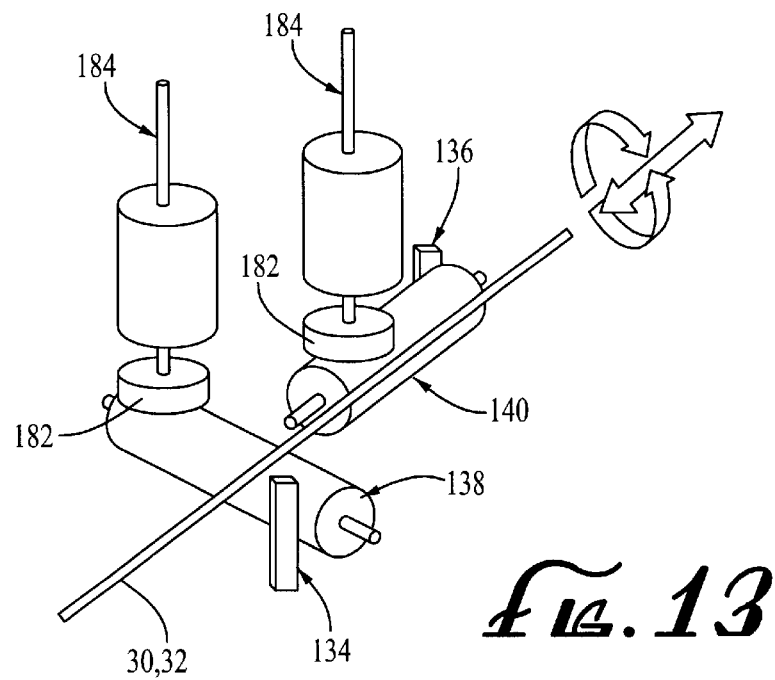
FIG. 13 shows an integrated arrangement for motion tracking and force feedback.

FIG. 13 is a modification of the arrangement shown in FIG. 9 further to include respective linear stepper motors (184) having the capability to cause the cushion (182) to engage the respective roller (138, 140) providing for integrated motion tracking and force feedback.

Software Driver

Figure 14:
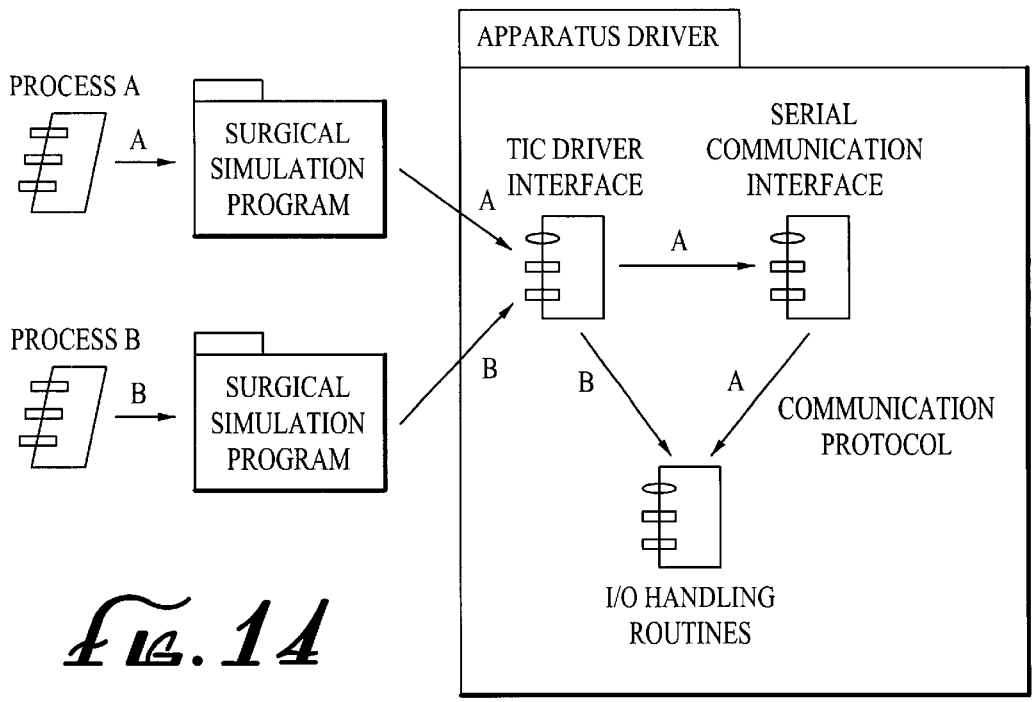
FIG. 14 shows a logical diagram of the driver software.

FIG. 14 is a component diagram illustrating the various software components effective to link operation of the TiC apparatus (10), the controller (60) and the surgical simulation apparatus (40). The apparatus driver represented is a low-level software unit that acts as an interface between the surgical simulation program and the TiC apparatus (10).

"Process A" in FIG. 14 represents the situation in which the surgical simulation program has executed in an external work station, such as the simulation apparatus (40) shown in FIG. 3. "Process B" in FIG. 14 represents the situation in which the surgical simulation program and the apparatus driver reside in the same computing resource.

Figure 15:
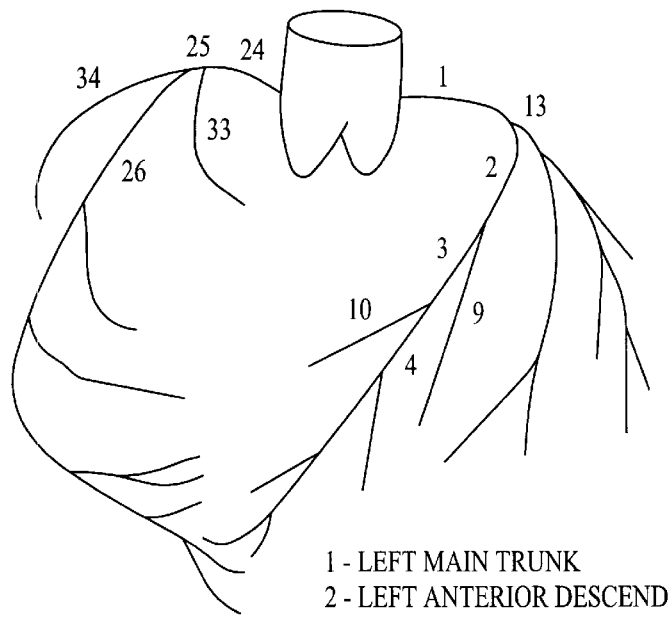
FIG. 15 shows a simulated tree of coronary vessels.

The objective of the device driver is to allow the calling functions in application program to control the apparatus and read data from it without the need to be involved in low level details regarding the serial communication between the workstation (40) and the controller (60). The driver software could be implemented as shown in FIG. 15.

The following code is a definition of the TiC Driver Interface class in C++.

```
class TicInterface
{
    private:
        int catheterDisplacement, catheterRotation;
        int guidewireDisplacement, guidewireRotation;
        int balloonInflateVolume;
        int stentReleaseFlag;
        int dyeContrastVolume, dyeContrastInjectRate;
        int zoomX, zoomY;
        int panX, panY;
        int rotateX, rotateY;
        int shutterX, shutterY;
        int contrast;
        int brightness;
        int resetFlag;
    public:
        ...
};
```

The Serial Communication class handles all the low level communication through the serial ports between the workstation (40) and the controller (60) of apparatus (10). A definition in C++ is shown as follows:

```
class Serial Communication
{
    private:
        int fd;      // file description of the port device
        int port;    // number of port opened
        int openSerialPort(int port, long baud, short bits);
        void closeSerialPort();
```

```
        int serialPacket(int fd, int numByte); // set number of bytes
  in a packet protected:
        Serial();
        ~Serial();
        int serialRead(char *buf, int bufLength); // read data of size
        bufLength
        int serialWrite(int inbuf);      // writing a byte to the serial
        port
};
```

When the Serial class is first initiated, the serial port is opened by calling the private function openSerialPort and serialPacket to set the number of bytes in the packet. The initialization fails on events such as the apparatus is not switched on or not connected to serial port. Upon successful initialization, the serial port is established as an I/O device of the workstation. The function serialRead will read bytes of data from the port while the function serialWrite writes to the port.

The objective of I/O Handling Routines is to access the values in various controls through a data acquisition board (e.g. the interface circuits (52,54)) and communication ports, such as the parallel port, MIDI port and serial ports of the controller (60), and then assemble these data into a single record to be transmitted to the workstation. The I/O Handling Routines consist of several portions: Parallel Port I/O Handling Module, MIDI Port I/O Handling Module, Serial Port Handling Module, Data Acquisition Module and Data Assembling Module.

If a single data acquisition board is not used or insufficient to handle all the input/output requirements, the following is a possible allocation of the communication ports assuming a typical PC configuration with 2 serial ports, 1 parallel port and 1 MIDI port. The Parallel Port I/O Handling Module takes charge of inputs from the parallel port. These are digital inputs for imaging control operation such as zooming and rotation. This module is also responsible for transmitting the signals to the stepper motor drivers (116,126) that are an external hardware circuit. The MIDI Port I/O Handling Module takes charge of analog inputs from the syringe for dye contrast injection, and setting pressure for ballooning. The Serial Port I/O Handling Module takes charge of the serial inputs from the catheter and guidewire encoders (112,122) in the tactile subsystem (52). The Serial Port I/O Handling Module is responsible for pushing the assembled record out to the workstation (40). The Data Assembling Module handles the formulation of the record from the inputs.

The communication link between the workstation and PC can be RS-232C with baud rate 9600, 8 bit data, 2 stop bits and without parity. When the workstation sends a byte 'P' to the apparatus, a 5-byte record is sent back by the device through the controller.

There may be situations where the catheter is pulled/rotated while the balloon is inflated/deflated, the guidewire is pulled/rotated, or the stent is deployed. Hence, it is necessary to interleave the various formats of data so that the workstation can obtain the latest information about all the variables. The MSB (Most Significant Byte) and LSB (Least Significant Byte) together will form a signed two-byte decimal value.

In normal situation, the 5-byte record should have the following formats:

Format 1 - Catheter displacement/rotation

This record tells the absolute displacement and rotation values of the catheter.

| | |
|---|---|
| Ascii 'A' | First Byte |
| MSB of Displacement | Second Byte |
| LSB of Displacement | Third Byte |
| MSB of Rotation | Fourth Byte |
| LSB of Rotation | Fifth Byte |

Format 2 - Guidewire displacement/rotation

This record tells the absolute displacement and rotation values of the guidewire.

| | |
|---|---|
| Ascii 'B' | First Byte |
| MSB of Displacement | Second Byte |
| LSB of Displacement | Third Byte |
| MSB of Rotation | Fourth Byte |
| LSB of Rotation | Fifth Byte |

Format 3 - Balloon inflation/deflation

This record tells whether the balloon has been inflated or deflated.

| | |
|---|---|
| Ascii 'C' | First Byte |
| MSB of Inflation | Second Byte |
| LSB of Inflation | Third Byte |
| MSB of Deflation | Fourth Byte |
| LSB of Deflation | Fifth Byte |

Format 4 - Stent deployment

This record tells whether the stent has been deployed or not.

| | |
|---|---|
| Ascii 'D' | First Byte |
| Binary 1 or 0 | Second Byte |
| Binary 0 | Third Byte |
| Binary 0 | Fourth Byte |
| Binary 0 | Fifth Byte |

When the second byte is binary 1, the stent is deployed. When the second byte is binary 0, the stent has not been deployed. The remaining 3 bytes are not used.

Format 5 - Dye contrast injection

This record tells whether the dye contrast injection has been activated.

| | |
|---|---|
| Ascii 'E' | First Byte |
| MSB of Volume of Contrast | Second Byte |
| LSB of Volume of Contrast | Third Byte |
| MSB of Injection Rate | Fourth Byte |
| LSB of Injection Rate | Fifth Byte |

Format 6 - Image zooming

This record tells whether image zooming has been activated.

| | |
|---|---|
| Ascii 'F' | First Byte |
| MSB of X Magnitude | Second Byte |
| LSB of X Magnitude | Third Byte |
| MSB of Y Magnitude | Fourth Byte |
| LSB of Y Magnitude | Fifth Byte |

Format 7 - Image panning

This record tells whether image panning has been activated.

| | |
|---|---|
| Ascii 'G' | First Byte |
| MSB of X Magnitude | Second Byte |
| LSB of X Magnitude | Third Byte |
| MSB of Y Magnitude | Fourth Byte |
| LSB of Y Magnitude | Fifth Byte |

Format 8 - Image rotation

This record tells whether image rotation has been avtivated.

| | |
|---|---|
| Ascii 'H' | First Byte |
| Values 0, 1, 2 | Second Byte |
| Binary 0 | Third Byte |
| MSB of Rotation Angle | Fourth Byte |
| LSB of Rotation Angle | Fifth Byte |

When the second byte is 0, the patient table has been rotated along X-axis. When the second byte is 1, the patient table has been rotated along Y-axis. When the second byte is 2, the patient table has been rotated along Z-axis.

Format 9 - Image contrast/brightness

This record tells whether image contrast/brightness control has been activated.

| | |
|---|---|
| Ascii 'I' | First Byte |
| MSB of Change in Contrast | Second Byte |
| LSB of Change in Contrast | Third Byte |
| MSB of Change in Brightness | Fourth Byte |
| LSB of Change in Brightness | Fifth Byte |

Format 10 - Shutter

This record tells whether shutter has been activated.

| | |
|---|---|
| Ascii 'J' | First Byte |
| MSB of X Magnitude | Second Byte |
| LSB of X Magnitude | Third Byte |
| MSB of Y Magnitude | Fourth Byte |
| LSB of Y Magnitude | Fifth Byte |

Format 11 - Roadmap

This record tells whether roadmap has been activated.

| | |
|---|---|
| Ascii 'K' | First Byte |
| Binary 0 or 1 | Second Byte |
| Binary 0 or 1 | Third Byte |
| Binary 0 or 1 | Fourth Byte |
| Binary 0 or 1 | Fifth Byte |

When the second byte is binary 0, roadmap channel 1 is selected otherwise channel 2 is selected. When the third byte is binary 1, play selected roadmap. When the fourth byte is binary 1, move to the next frame of selected roadmap. When the fifth byte is binary 1, move to the previous frame of selected roadmap.

Format 12 - Reset

This record tells whether reset has been activated.

| | |
|---|---|
| Ascii 'L' | First Byte |
| Binary 0 | Second Byte |
| Binary 0 | Third Byte |
| Binary 0 | Fourth Byte |
| Binary 0 | Fifth Byte |

The application program should set parameters to default upon receipt of this record.

Format 13 - Pause

This record tells whether catheter and guidewire manipulation has been suspended.

| | |
|---|---|
| Ascii 'M' | First Byte |
| Binary 0 | Second Byte |
| Binary 0 | Third Byte |
| Binary 0 | Fourth Byte |
| Binary 0 | Fifth Byte |

Format 14 - Resume

This record tells the application program that the pause of catheter/guidewire manipulation is resumed.

| | |
|---|---|
| Ascii 'N' | First Byte |
| Binary 0 | Second Byte |
| Binary 0 | Third Byte |
| Binary 0 | Fourth Byte |
| Binary 0 | Fifth Byte |

The Pause and Resume records are necessary to add more length to the catheter and guidewire needed in the simulation.

Format 15 - No reset

If there has been no event, the following record will be transmitted.

| | |
|---|---|
| Ascii 'O' | First Byte |
| Binary 0 | Second Byte |
| Binary 0 | Third Byte |
| Binary 0 | Fourth Byte |
| Binary 0 | Fifth Byte |

Format 16 - Error/exception event

If there is an error or exception detected by the controller, the following record will be transmitted.

| | |
|---|---|
| Ascii 'X' | First Byte |
| MSB of Code | Second Byte |
| LSB of Code | Third Byte |
| MSB of Control ID | Fourth Byte |
| LSB of Control ID | Fifth Byte |

Both second and third bytes contribute to the error/exception code. The fourth and fifth bytes indicate the control that has generated the error. Binary 0 in the last 4 bytes can be used to tell an error or exception that is not recognized or the control that has generated this error or exception is not known.

Force feedback is handled in the following manner. The application program that resides on the workstation will compute the contact force. This force is transmitted to the apparatus in the following records that are transmitted from workstation to controller.

Format 17 - Force feedback (push/pull)
This record tells the opposite force along the axis of catheter or guidewire when the catheter or guidewire has been pushed forward or pulled backward. The opposite force is the feedback on the tactile subsystem of the apparatus.

| | |
|---|---|
| Ascii 'N' | First Byte |
| Binary 0, 1 | Second Byte |
| Binary 0, 1 | Third Byte |
| MSB of Change in Force | Fourth Byte |
| LSB of Change in Force | Fifth Byte |

The binary 0 and 1 in the second byte imply catheter and guidewire respectively. The binary 0 and 1 in the third byte imply that catheter/guidewire has been pushed forward and pull backward respectively.

Format 18 - Force feedback (rotate)
This record tells the opposite moment along the axis of catheter or guidewire when the catheter or guidewire has been rotated left or right. The opposite moment is the feedback on the tactile subsystem of the apparatus.

| | |
|---|---|
| Ascii 'Q' | First Byte |
| Binary 0, 1 | Second Byte |
| Binary 0, 1 | Third Byte |
| MSB of Change in Moment | Fourth Byte |
| LSB of Change in Moment | Fifth Byte |

The binary 0 and 1 in the second byte implies catheter and guidewire respectively. The binary 0 and 1 in the third byte implies that catheter/guidewire has been rotated left or right respectively.

The workstation (40) sends a byte ascii 'T' to the apparatus to shut down the handling routines resided in the controller. The workstation sends a byte ascii 'R' to the apparatus to set parameters in the handling routines resided in the controller to default values. The workstation sends a byte ascii 'C' to the apparatus to clear the transmission buffer in the controller.

Surgical Simulation

It is necessary to build a realistic and accurate vasculature of human anatomy for computer simulation of catheterization procedures. The human primary vasculature, cardiac, cerebral and other secondary tertiary networks are used to create the simulated vasculature of a virtual patient. All the blood vessels are assumed as cylindrical structures with circular-ring cross-sections of various radii. A central line model is used to characterize the segments of the vasculature. With this model, a segment of blood vessel is represented by a set of 3D points along its central line with associated radii. The central line for this segment can then be interpreted into, for example, a linear format by simply joining any two adjacent points with a straight line or a first order continuity curve by smoothing any three points with a Hermite function. Higher order continuity can also be obtained with more points in the interpretation depending on the purposes of applications. In the following, the construction of the central line models for primary aorta, coronary, cerebral and other secondary tertiary networks are discussed. It is noted that they are from different sources and have been fused and co-registered with the VHD™ fluoroscopic images in the world-coordinate space. A segment of blood vessel is defined by any two adjacent branching joints in this central line model.

The Primary Aorta: The primary arterial vasculature is reconstructed from known photo data. The Visible Human (VHD)™ data are stored in numerous 2D slices of uniform thickness of 1 mm. The contours of the blood vessels at the region of interest are first manually segmented at each slice with Photoshop™, a commercial program. The center of the projected cross-section of a vessel is then calculated and the resultant coordinates of this center point are taken as the coordinates of the center of the vessel at this slice. The corresponding radius of the vessel is obtained by the following equation: $\pi R^2 = A \cdot \cos\alpha$, where R is the radius, A is the cross area of the vessel at this slice, and $\alpha$ is the projection angle which can be obtained by using the relationship between the coordinates of the central line points at adjacent slices. The 3D central line is built for the vessel by connecting all the coordinates at the slices involved. This primary structure serves as a roadmap to extend the arterial model by adding of secondary and tertiary networks from other scanned data sets.

The Coronary Vessels: It is found that the coronary vessels in the VHD™ photo data are mostly collapsed due largely to the fact that no blood flow and pressure were in the vessels of the cadaver and they were squeezed by the surrounding muscles. A professional steel model is therefore employed to construct a 3D model of the cardiac vessels by using Coordinate Measuring Machine (CMM) Probing. A CMM equipped with an analogue probe or touch probe is a prominent example of the contact inspection method used to determine the 3D coordinates of a model. It ranges from the right coronary artery to the atrioventricular branch, from the left main trunk to the left anterior descending branch and the left circumflex branch. The vessels are considered to be the principal sites for the interventional cardiology practice. The CMM machine measures the related coordinates of points along the central line. The related radii of the vessels are also found by using a mechanical measuring technique. The determined coordinates and radii are then fed into a process to rebuild the coronary vessel structure. The shape of the vascular system has been examined and refined further by the medical professional using an editor tool.

The Cerebral Vessel Model: An interactive vessel tracing method is used to obtain the cerebral model in this study. Volume data sets often lack the resolution to allow automatic network segmentation for blood vessels. This approach provides a free-form curve drawing technique by which human perception is quantitatively passed to the computer, using the reach-in environment of the Virtual Workbench. The precise and dextrous environment transform perception to easy identification of vessels. The tools exploit the reach-in hand-immersion ergonomics of the Virtual Workbench to allow sustained productive work and 3D-textures subvolumes to allow interactive vessel tracing in real-time. A set of magnetic resonance angiograph (ERA) data of human brain is used for this purpose and a total of 251 segments of the cerebral vessels are identified and registered based on the connection with the primary vasculature of the VHD™ data.

The Simulated Vasculature of Human Anatomy: A realistic and accurate vasculature of human anatomy has therefore been achieved for computer simulation for catheterization procedures based on models of primary, coronary, cerebral and other secondary tertiary networks developed. There are a total of 394 segments for the entire vasculature. Among them, the cardiac model has 41 segments while the cerebral model has 251. The vasculature anatomy is represented by a topological hierarchy structure of the central lines, their corresponding radii and the neighborhood connecting relations of the vessels. These vessels are assumed as cylindrical structures with varying radii.

Topological Hierarchy Structure: The topology of vasculature is very helpful in speeding up the computational analysis of catheter navigation. The topological hierarchy structure can be generated by using the information of coordinates and radii of the central line model of the vessels, and the relationship between neighboring vessel segments. This hierarchy specifies the connection of adjacent vessels with a tree structure. FIG. 15 shows this tree of the coronary vessels based on the information from the professional model. Each vessel is named as a segment labeled with its index in this structure. It uses a parent-child relationship between a vessel segment with its adjacent vessels/segments. The numbering starts from the left coronary artery as shown in this drawing.

Figure 16:
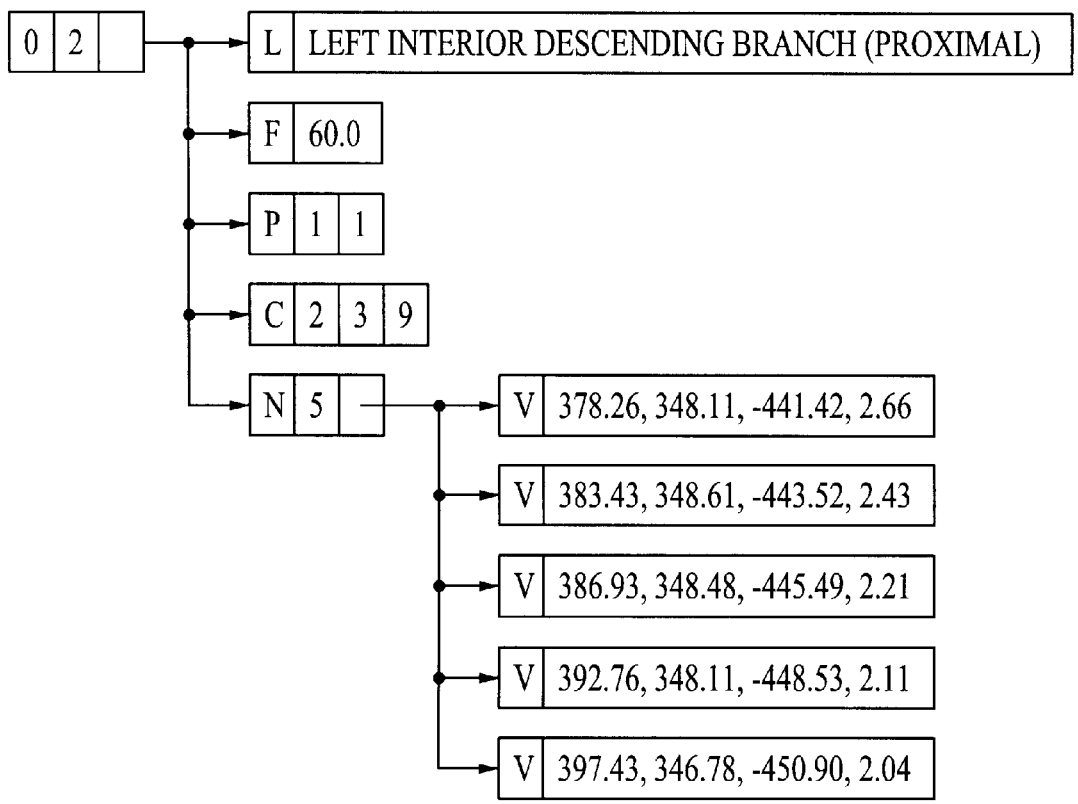
FIG. 16 shows a data structure for the topographical hierarchy of the coronary vessel tree.

FIG. 16 shows an example of the data structure for a vessel segment of the coronary tree. The left anterior descending branch (proximal) is recorded as a segment in this 3D hierarchy data structure of the coronary vessel system. The G at the first row indicates the segment number; L at the first row refers to the description of the segment; P at the third row indicates its parent (there is only one parent in this case, left main trunk. The parent segment number is 1); C at the fourth row indicates its children (two children in this cases: segment no. 3, left anterior descending branch (mid), and no. 9, $1^{st}$ diagonal branch (D1)); N at the fifth row indicates number of its central line points. The first three real numbers in the right side of the $5^{th}$ row to the last row are the x, y and z coordinates of the central points while the last number refers to the corresponding radii. They are all in millimeter.

The Physics of Catheter Navigation: With the goal of creating a realistic real time interactive environment for the analysis of catheter navigation in the vascular structure, an incremental Finite Element Method has been applied to the analysis of catheter navigation. In this FEM analysis, the blood vessels are assumed as rigid circular tube-structures with various radii. The present method can be extended to more realistic vessels with arbitrary cross-sections and deformabilities.

Figure 17:
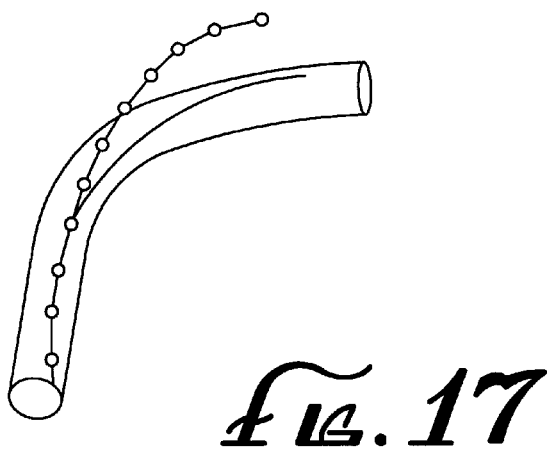
FIG. 17 shows a 3D beam element model of a blood vessel.

It is commonly accepted that most of the blood vessels are well stretched by the surrounding muscles and therefore the vasculature network is hardly deformed. It is also true that the tip of a guidewire or navigating catheter is very soft in order to prevent to damage the blood vessel when in contact. The vessel wall is relatively, therefore, stiffer and it is quite reasonable to assume them as rigid during the interaction with catheters. On the other hand, typical catheters/guidewires have curved/uncurved slender cylinders geometry (the cross-sections of catheters/guidewires are generally in circular or circular ring form) and can be discretized into 3D beam elements. Thus, they can be considered as systems of flexible multiple bodies as shown in FIG. 17. Those elements connected with each other at the nodes are capable of describing the deformation modes of extension, compression, bending and torsion. The catheter navigation, therefore, can be considered as a sequence of movements of the flexible multibody systems inside the rigid tube-structures.

These multibody systems are subjected to single or combined push/pull/twist at their extreme ends as the external inputs. The movement of the catheter is assumed as the sum of rigid-body displacements and deformations at each step because the deformations are relatively small compared to the rigid-body displacements. Hence, it is logical to treat the elements of the catheter system as rigid bodies first and then find the deformations at their equilibrium position. Next, a variational principle is developed based on the virtual work method to derive the formulations of multibody dynamics method (MDM). The MDM models the kinematics (rigid body displacements) of the multibody system. The finite element method models the deformations of the flexible bodies or the analysis of catheter navigation. It is noted that a nonlinear FEM is applied here since the catheters generally undergo large deformations.

The Governing Equation: Consider a catheter that is discretized into elements with a deformed configuration. This flexible multibody system is in dynamic equilibrium with the applied forces, contact traction and internal forces at time t. Two coordinate systems are used to describe the movement and the deformations of the catheter system. The coordinate system XYz is the inertial (global) reference frame and xyz is the body (local) reference frame at time t.

The variational equations of motion of the catheter system is given as $$\int_S \delta \vec{u}^T \vec{T} dS - \int_V \delta \vec{u}^T (\rho \ddot{\vec{u}} - \vec{f}) dV = \int_V \delta \vec{\epsilon} (\vec{\sigma} - \vec{\sigma}^0) dV \quad (1)$$

where

S denotes the boundary surface and V denotes the volume of the catheter.

$\vec{u}$ denotes the displacement vector of a catheter point at time t.

$\vec{\epsilon}$ and $\vec{\sigma}$ denote the strain vector and stress vector, respectively.

$\vec{\sigma}^0$ (denotes the residual stress vector due to the accumulation of the previous deformations which can be reduced through a process of energy release (shape recover).

$\delta \vec{u}$ denotes the virtual displacement vector that is consistent with the constrain conditions $\delta \vec{\epsilon}$ denotes the corresponding virtual strain vector.

$\rho$ denotes the mass density of the catheter and $\vec{f}$ denotes the body force vector.

$\ddot{u}$ denotes the acceleration vector (second order differentiation of variables with respect to time t).

T is the traction vector and can be expressed in terms of the external force applied at the boundary S and the contact force between the catheter and the walls of the vessels.

Let us define the displacement vector as a summation of two terms, a rigid body displacement and a deformation, in order to derive the explicit formulation for the equation of solution for the catheter movement. Realizing that the rigid displacement results in no strain and stress, we then can formulate the final two variational equations from (1) as $$\int_S \delta \vec{u}_r^T (\vec{T}_a + \vec{T}_c) dS - \int_V \delta \vec{u}_r^T (\rho \ddot{\vec{u}}_r - \vec{f}) dV = 0 \quad (2)$$

for determining the moving of the multibody system with each element moving as a rigid object and $$\int_S \delta \vec{u}_f^T (\vec{T}_a + \vec{T}_c) dS - \int_V \delta \vec{u}_f^T (\rho \ddot{\vec{u}}_r - \vec{f}) dV = \int_V \delta \vec{\varepsilon}_f (\vec{\sigma}_f - \vec{\sigma}^0) dV \quad (3)$$

where $\vec{u}_r$ denotes the rigid displacement; $\vec{u}_f$ is for the deformation, $\vec{T}_a$ and $\vec{T}_c$ are for the external force and the contact force, respectively; and $\vec{\varepsilon}_f$ and $\vec{\sigma}_f$ for the strain and stress corresponding to the deformation. It is assumed here that the deformations are generally smaller comparing to the rigid displacements. The deformation can then be assumed as time independent during the navigation. The acceleration of the deformations has therefore been neglected in the formulation.

FEM Formulation: 3D beam elements are used in this study to derive the equation of solution in the FEM analysis of the catheter navigation. The variational equations (2) and (3), hence, can be rewritten for the catheter with N elements as $$\sum_{n=1}^{N} \int_{S_n} \delta \vec{u}_r^T (\vec{T}_a + \vec{T}_c) dS - \sum_{n=1}^{N} \int_{V_n} \delta \vec{u}_r^T (\rho \ddot{\vec{u}}_r - \vec{f}) dV = 0 \quad (4)$$

for the rigid body moves of the beam elements and $$\sum_{n=1}^{N} \int_{S_n} \delta \vec{u}_f^T (\vec{T}_a + \vec{T}_c) dS - \sum_{n=1}^{N} \int_{V_n} \delta \vec{u}_f^T (\rho \ddot{\vec{u}}_r - \vec{f}) dV = \sum_{n=1}^{N} \int_{V_n} \delta \vec{\varepsilon}_f^T (\vec{\sigma}_f - \vec{\sigma}^0) dV \quad (5)$$

for the deformations of the elements. In which $S_n$ and $V_n$ denote the boundary and volume of the nth element, respectively.

We then have the matrix equations of solution resulted from the equation (4) and (5) through a common FEM procedures as $$\vec{M}\ddot{\vec{U}} = \vec{T}_a + \vec{T}_c + \vec{f} \quad (6)$$

$$\vec{K}\vec{u} = \vec{T}_a + \vec{T}_c - \vec{M}\ddot{\vec{U}} + \vec{f} + \vec{\delta}^0 \quad (7)$$

for the multidynamics analysis of the rigid body moves and for the FEM analysis of the deformations. In which the rigid body displacement vector $\vec{u}$ is defined in terms of three translations and three rotations at each FEM node while the deformation vector $\vec{U}$ is also expressed in the same way with a total of six degrees of freedom at a FEM node. The matrices $\vec{M}$ and $\vec{K}$ are called the global mass matrix and the global stiffness matrix, respectively. It is noted that the equations (6) and (7) are coupled with each other. We have come with a semi-implicit iteration method to solve them effectively.

Contact Analysis: Contact analysis contributes a significant proportion of the FEM computation time. The hierarchy of the vasculature of human anatomy is employed to guide the contact search of the navigating catheter/guidewire with respect to a group of vessels involved.

Topology Supported FEM Catheter Navigation Analysis: A semi-implicit method, based on the topological hierarchy of vasculature for the inside/outside checking and the computation of the contact force in the FEM analysis is disclosed. The method can be expressed as following execution routine and as shown in FIG. 16:

Step 1: Solve the multibody dynamic equation at each time step to move the catheter as a rigid multibody system. We used a slide technique based on their tangents to make a reasonable guess for the moving directions of the elements. The FEM elements of the catheter, with this method, move along their tangential directions as their rigid body movements.

Step 2: Conduct the inside/outside checking for each node at portion of the catheter under consideration. With the derived topological hierarchy of the vasculature, we need only to check one FEM node of the catheter with respect to its associated vessel segment and the vessels that have relative relations (through the defined parent-child topological relationship). By doing so, we drastically reduce the computation time for inside/outside checking as well as the computation of the related contact forces when some nodes are outside the vessel.

Step 3: If all catheter nodes are inside of the vessels, then go to Step 1; Otherwise, if at least one node is outside the vessels: compute the contact force at those FEM nodes according to $\vec{J} = cd\vec{n}$; where c is an adaptive coefficient determined through an interaction procedure. It is noted that the value of the coefficient c should reflect the material properties of the catheter and the vessels. However, we have to use an alternative way to determine its value due to the assumption we made for the vessels that all of them are treated as rigid. Here d denotes the distance and $\vec{n}$ denotes the force direction/unit vector of a node, respectively.

Step 4: Generate the stiffness matrix and associated force vectors for the catheter with respect to its new position, and impose the constraint conditions.

Step 5: Solve the FEM equation for the deformation of the catheter subject to the contact force. Update the catheter position and then go to Step 2.

The foregoing describes a number of embodiments of the present invention, and modifications, obvious to one skilled in the art can be made thereto without departing from the scope of the present invention.

We claim:

1. Apparatus for use in simulated image guided surgery, comprising:

positional transducer means responsive to a thin flexible member that can be manipulated by a user, the flexible member being of two parts, one sliding within the other in the form of a catheter and guidewire, the transducer means producing signals representative of displacement and rotation of said flexible member, said signals being representative of displacement and rotation of said catheter and representative of displacement and rotation of said guidewire;

clamping means located proximate said transducer means, and operable to respond to a controlling signal to apply a predetermined variable clamping force to the flexible member; and processor means receiving said displacement and rotation signals, and programmed to plot the path of the flexible member therefrom as it is manipulated by the user, and to produce said controlling signal in response to the instantaneous position along the path.

2. The apparatus of claim 1, wherein the positional transducer means comprises a rolling ball engaging the flexible member and further engaging two orthogonally arranged rotary encoders that generate the respective displacement and rotation signals.

3. The apparatus of claim 1, wherein the positional transducer means comprises two roller and encoder assemblies, each arranged orthogonally to the other, and engaging the flexible member, the respective encoder generating the respective displacement and rotation signals.

4. The apparatus of claim 2 or 3, wherein the positional transducer means comprises opposed clamp members and an actuator, the actuator being operable in response to the controlling signal to cause relative movement of the clamp members to apply or reduce the clamping force.

5. The apparatus of claim 4, wherein the actuator is a stepper motor, a servo-motor, or a linear motor.

6. The apparatus of claim 3, wherein said clamping means comprises a pair of cushions means connected to a respective actuator, each cushion means being engageable with a respective said roller, under control of the respective actuator, to apply or reduce the clamping force.

7. The apparatus of claim 1, wherein the positional transducer means and clamping means are separate and each is responsive to a respective one of the catheter and the guidewire, and wherein the processor plots the path of both the catheter and the guidewire and controls the clamping force applied to each.

8. The apparatus of claim 1, wherein at least said transducer means and said clamping means are housed within an enclosure, and said enclosure has an external opening through which said flexible member can be received.

9. The apparatus of claim 8, wherein said enclosure is a component of a manikin.

10. The apparatus of claim 1, further comprising display means, coupled to the processor means, displaying an image of the instantaneous position of the flexible member and/or a section of the total path taken from a stored record accessed by said processor means.

11. The apparatus of claim 10, further comprising activation means, coupled to the processor means, in operation causing the selective display of the instantaneous position or said section of the total path.

12. A system for the simulation of image guided surgery, comprising:
    a thin flexible member that can be manipulated by a user, the flexible member being of two parts, one sliding within the other in the form of a catheter and guidewire;
    positional transducer means responsive to said flexible member to produce signals representative of displacement and rotation of said flexible member, said signals being representative of displacement and rotation of said catheter and representative of displacement and rotation of said guidewire;
    clamping means locating proximate said transducer means, and operable to respond to a controlling signal to apply a predetermined variable clamping force to the flexible member;
    processor means receiving said displacement and rotation signals, and programmed to plot the path of the flexible member therefrom as it is manipulated by the user and to produce said controlling signal in response to the instantaneous position along the path taken from a predetermined simulation of the path; and
    display means, coupled to the processor means, to display an image of at least the instantaneous position of the flexible wire therealong.

13. The system of claim 12, further comprising at least one input device, coupled to the processor means, operable to cause the path to be displayed.

14. The system of claim 13, wherein said input device is a foot operated switch.

15. The system of claim 12, further comprising an input device, coupled to the processor means, operable to cause an image of a portion of the path to be displayed.

16. The system of claim 12, further comprising an input device to the processor means simulating a syringe, comprising a hand operable plunger mechanically connected with a transducer to provide an electrical signal representative of displacement of said plunger.

17. The system of claim 16, wherein said syringe transducer provides an electrical signal representative of rate of displacement.

18. The system of claim 15, wherein the simulated syringe includes resistive means operable under control of the processor means, to provide a predetermined resistive force to the plunger.

19. The system of claim 12, wherein at least said transducer means and said clamping means are housed within an enclosure, and said enclosure has an external opening through which said flexible member can be received.

20. The system of claim 19, wherein the enclosure further includes input control devices mounted on an external surface thereof, and coupled to the processor means.

21. The system of claim 20, wherein the input control devices are effective to cause the processor means to control operation of images displayed on the display means.

22. The system of claim 21, wherein the display devices comprise at least two monitors, a first displaying an image of the instantaneous position of the flexible member, and a second displaying image of at least a portion of the total path taken from a stored record accessed by said processor means.

23. The system of claim 22, wherein said displayed images are simulated x-ray, cine or fluoroscopic images.

24. The system of claim 12, wherein the positional transducer means comprises a rolling ball engaging the flexible member and further engaging two orthogonally arranged rotary encoders that generate the respective displacement and rotation signals.

25. The system of claim 24, wherein the positional transducer means comprises two roller and encoder assemblies, each arranged orthogonally to the other, and engaging the flexible member, the respective encoder generating the respective displacement and rotation signals.

26. The system of claim 24 or 25, wherein the positional transducer means comprises opposed clamp members and an actuator, the actuator being operable in response to the controlling signal to cause relative movement of the clamp members to apply or reduce the clamping force.

27. The system of claim 26, wherein the actuator is a stepper motor, a servo-motor, or a linear motor.

28. The system of claim 25, wherein said clamping means comprises a pair of cushions means connected to a respective actuator, each cushion means being engageable with a respective said roller, under control of the respective actuator, to apply or reduce the clamping force.

29. The apparatus of claim 12, wherein the positional transducer means and clamping means are separate and each is responsive to a respective one of the catheter and the guidewire, and wherein the processor plots the path of both the catheter and the guidewire and controls the clamping force applied to each.

30. The system of claim 12, wherein the processor means includes a memory that stores a plurality of images relating to vasculature available for display on the display means and a mathematical model of said vasculature from which said controlling signal is derived.

31. The system of claim 30, wherein the mathematical model is based on an incremental Finite Element Method technique.

32. A system for the simulation of image guided surgery, comprising:

a guidewire slidably contained within a catheter, each of which can be separately manipulated by a user;

two positional transducer means responsive to said guidewire and said catheter respectively, and producing separate signals, one of said signals being representative of displacement and rotation of said catheter and another of said signals being representative of displacement and rotation of said guidewire;

clamping means located proximate each said transducer means, and operable to respond to a respective controlling signal to apply a predetermined variable clamping force to the guidewire or catheter;

processor means receiving said displacement and rotation signals, and programmed to plot the path of guidewire and the catheter as they are separately manipulated by the user and to produce said controlling signals in response to the instantaneous position along the path taken from a predetermined simulation of the path;

display means coupled to the processor means, to display an image of the instantaneous position of the guidewire and catheter and an image of at least a portion of said path; and input devices, coupled to said processor means, by which a user, can cause display of an image of the instantaneous position or the portion of the path.

33. A method for the simulation of image guided surgery, the method comprising the steps of:

transducing the displacement and rotation of a catheter and transducing the displacement and rotation of a guidewire, the guidewire sliding within the catheter and the guidewire and catheter being parts of a thin flexible member manipulated by a user;

plotting the path of the flexible member along a simulated path representing vasculature;

user selectably displaying an image of the instantaneous position of the flexible member along the path and/or a portion of the path; and applying a predetermined variable clamping force to the flexible member in accordance with the instantaneous position of the flexible member.

34. The method of claim 33, whereby the flexible member comprises two independent components and the steps of transducing, plotting, displaying and applying a clamping force occur for each of the components.

35. The method of claim 34, comprising the further step of receiving an input from a device representative of syringe activation, and causing said activation to be displayed.

36. The method of claim 35, comprising the further step of applying a predetermined clamping force to the device.

37. The method of claim 33, comprising the further steps of:

storing a plurality of images relating to vasculature as said images to be displayed;

storing a mathematical model of the vasculature; and calculating a controlling signal to control said clamping force.

38. The method of claim 37, whereby said mathematical model is based on an incremental Finite Element Method technique.

* * * * *